US006259095B1

United States Patent
Bouton et al.

(10) Patent No.: US 6,259,095 B1
(45) Date of Patent: Jul. 10, 2001

(54) SYSTEM AND APPARATUS FOR DETECTING AND LOCATING SOURCES OF RADIATION

(75) Inventors: Chad E. Bouton; Daniel A. Kramer, both of Dublin; Richard C. Mayoras, Jr., Hilliard, all of OH (US)

(73) Assignee: Neoprobe Corporation, Dublin, OH (US)

( * ) Notice: Subject to any disclaimer, the term of this patent is extended or adjusted under 35 U.S.C. 154(b) by 0 days.

(21) Appl. No.: 09/178,322

(22) Filed: Oct. 23, 1998

(51) Int. Cl.$^7$ ........................................................ A61B 6/00
(52) U.S. Cl. .................................. 250/336.1; 250/370.06; 250/369
(58) Field of Search ............................ 250/336.1, 370.06, 250/369

(56) References Cited

U.S. PATENT DOCUMENTS

| | | |
|---|---|---|
| 4,782,840 | 11/1988 | Martin, Jr. et al. . |
| 4,801,803 | 1/1989 | Denen et al. . |
| 4,889,991 | 12/1989 | Ramsey et al. . |
| 4,893,013 | 1/1990 | Denen et al. . |
| 5,070,878 | 12/1991 | Denen . |
| 5,151,598 | 9/1992 | Denen . |
| 5,246,005 | 9/1993 | Carroll et al. . |
| 5,383,456 | 1/1995 | Arnold et al. . |
| 5,429,133 | 7/1995 | Thurston et al. . |
| 5,475,219 | 12/1995 | Olson . |
| 5,482,040 | 1/1996 | Martin, Jr. . |
| 5,732,704 | 3/1998 | Thurston et al. . |

OTHER PUBLICATIONS

Morton, et al. "Technical Details of Intraoperative Lymphatic Mapping for Early Stage Melanoma," *Arch. Surg.* 1992; 127: 392–399.

Uren, et al, "Lymphoscintigraphy in High–Risk Melanoma of the Trunk: Predicting Draining Node Groups, Defining Lymphatic Channels and Locating the Sentinel Node," *J. Nucl Med* 1993; 34:1435–1440.

Guiliano, et al., "Lymphatic Mapping and Sentinel Lymphadenectomy for Breast Cancer," Annals of Surgery, vol. 220, No. 3: 391–401, 1994, J.B. Lippincott Company.

Greenson, et al, "Identification of Occult Micrometastases in Pericolic Lymph Nodes of Dukes' B Colorectal Cancer Patients Using Monoclonal Antibodies against Cytokeratin and CC49," *Cancer* 1994; 73: 563–569.

Bertsch, et al, "Radioimmunoguided Surgery System Improves Survival for Patients with Recurrent Colorectal Cancer," *Surgery* 1995; 118: 634–639.

Arnold, et al, "Radioimmunoguided surgery in Primary Colorectal Carcinoma: An Intraoperative Prognostic Tool and Adjuvant to Traditional Staging," *American J. Surg.* 1995; 179: 315–318.

Scheebaum, et al, "The Significance of Intraoperative Periportal Lymph Node Metastasis Identification in Patients with Colorectal Carcinoma," *Cancer*, 1995; 75: 2809–2817.

Cote, et al, "Intraoperative Detection of Occult Colon Cancer Micrometastases Using 125I–Radiolabeled Monoclonal Antibody CC49," *Cancer* 1996; 77:613–620.

*Primary Examiner*—Constantine Hannaher
*Assistant Examiner*—Andrew Israel
(74) *Attorney, Agent, or Firm*—Mueller and Smith, LPA

(57) ABSTRACT

System and apparatus for locating sources of radiation emanating from predetermined radionuclides. The apparatus incorporates a large window display utilizing icon imagery to identify counting functions such as target count and background. A variety of radionuclide modes of operation can be selected by the operator and the system automatically defaults to detector bias selection and window reference voltage selection in correspondence with the elected radionuclide. A bar graph readout apprises the user of the amount of time or count level remaining in a target or background procedure and the flashing of icon identifiers occurs during such procedures. Pulse validation is improved by the utilization of a discriminator which evaluates pulse width.

25 Claims, 16 Drawing Sheets

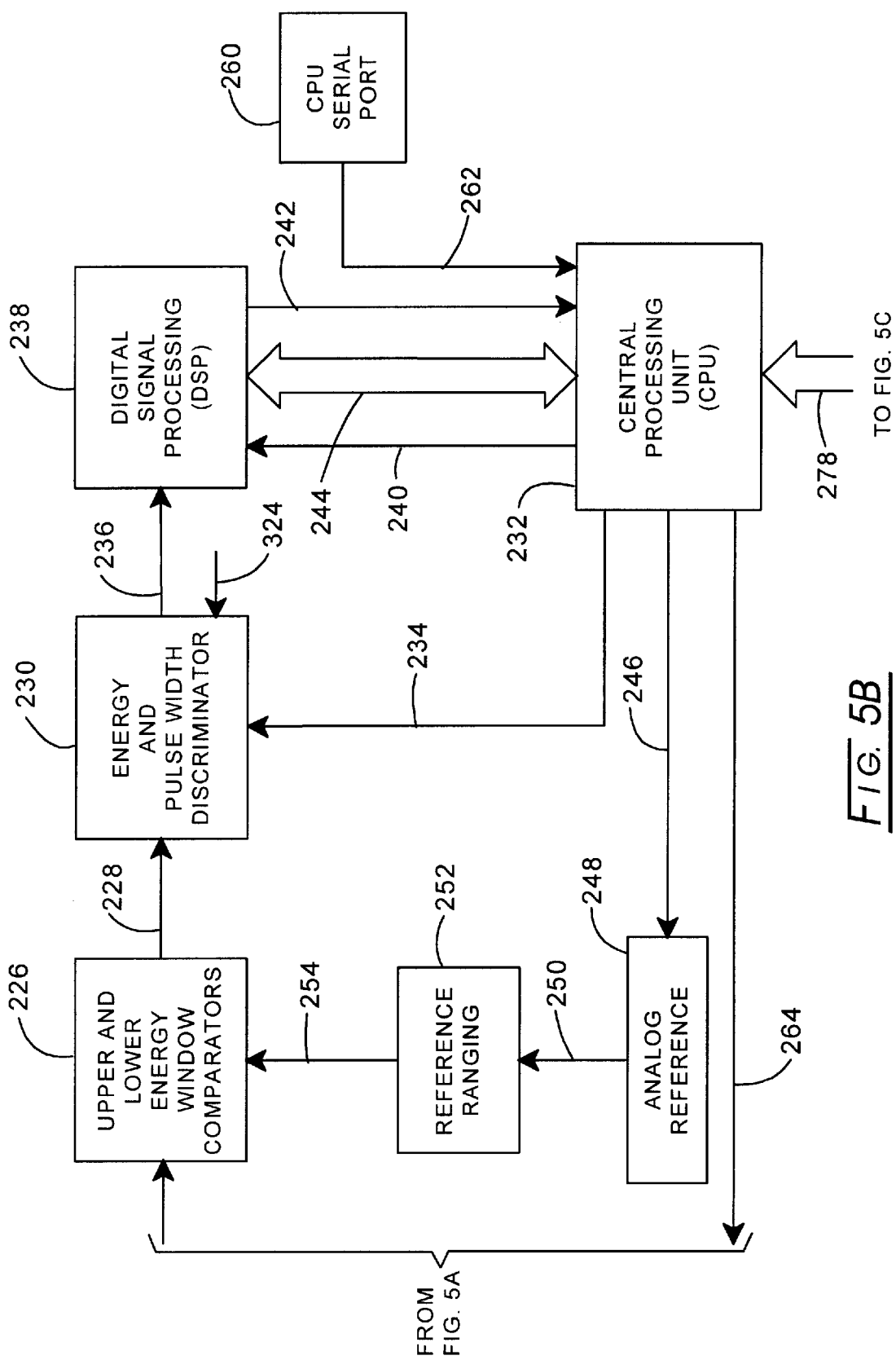

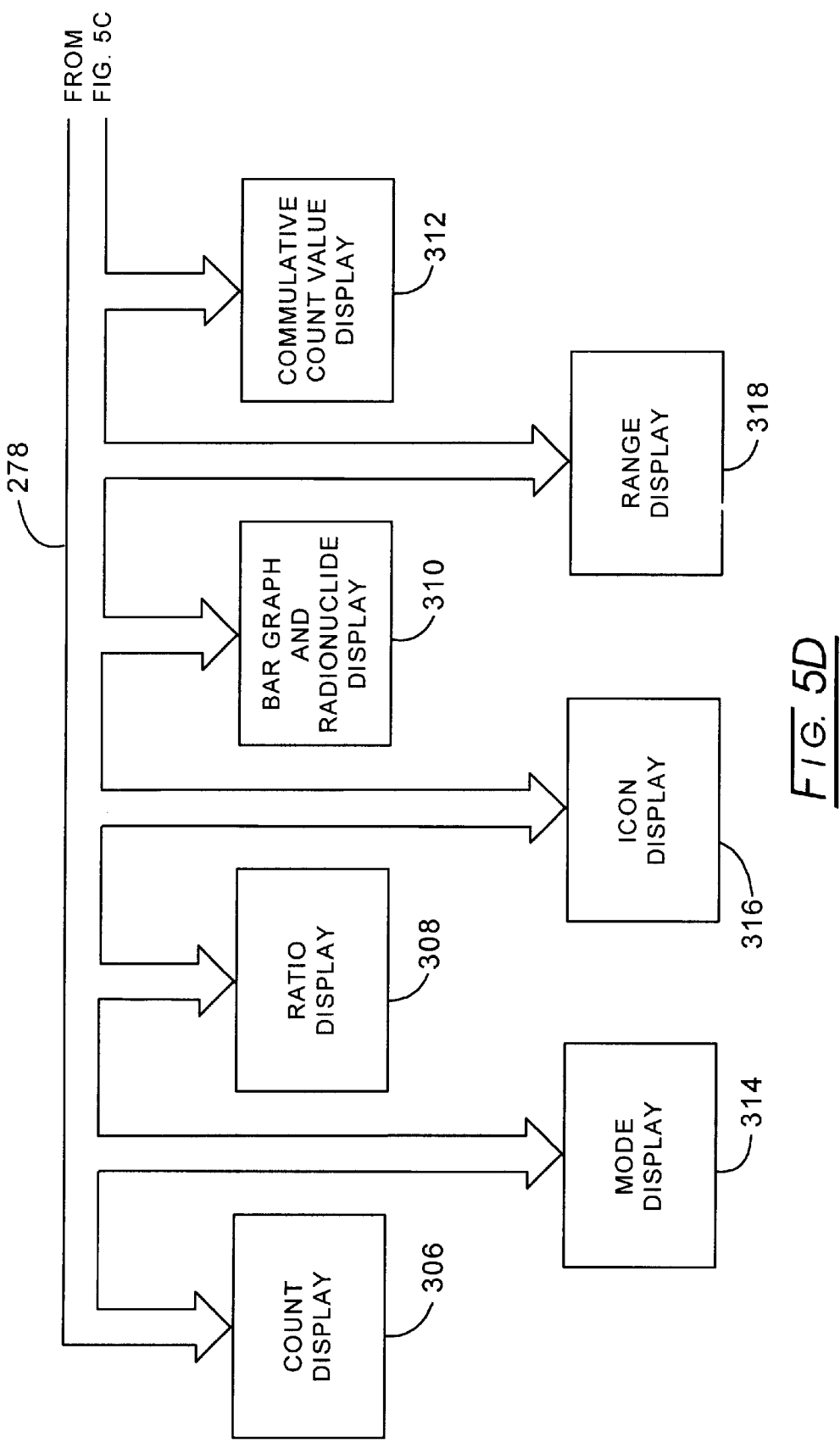

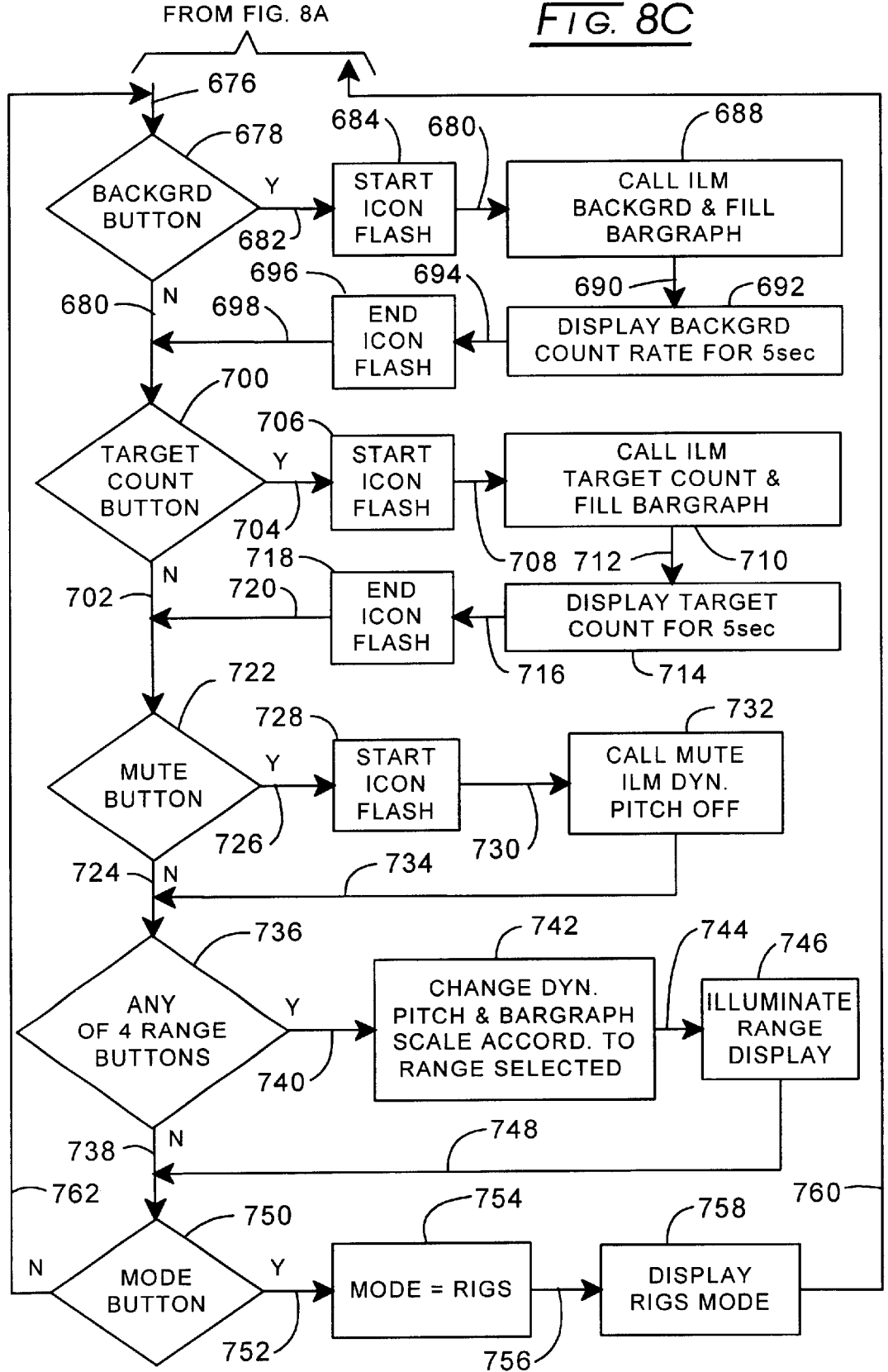

SYSTEM AND APPARATUS FOR DETECTING AND LOCATING SOURCES OF RADIATION

STATEMENT REGARDING FEDERALLY SPONSORED RESEARCH

Not applicable.

BACKGROUND OF THE INVENTION

Current and historical procedures for treatment of colon and rectal cancer generally have been based upon the natural history of tumor spread, and thence, upon operative and non-operative options available to the practitioner. Operative options generally have looked to the physical identification and surgical resection of tumor. A variety of techniques have been brought to bear in the art with the purpose of aiding the surgeon in detecting and localizing neoplastic tissue as part of this surgical procedure. ("Neoplastic tissue," for the present purposes, often is referred to as cancerous tissue, though malignant tumor and malignant tumor cells also are found in the terminology of the art. The term "neoplastic tissue" includes all of these.) A substantial amount of the effort which has been expended in seeking to aid the surgeon in the process of locating neoplastic tissue has been concerned with the utilization of radiolabeled antibody. For example, one technique includes the scintillation scanning of patients who have been injected with relatively high energy, e.g. $^{131}I$ labeled antibodies. Such photoscanning scintigrams are difficult to interpret because of blood pool background radioactivity. Computer subtraction of radioactive blood pool agents and the use of two labeled antibodies (one specific for the tumor and one nonspecific) have been attempted in an effort to enhance imaging. Nevertheless, such techniques have been found to provide little, if any, useful information to the surgeon, especially over and above the CAT scan, magnetic resonance imaging, and like traditional techniques. Typically, large tumor is readily located by the surgeon by visualization at the operating theater, and, in particular, through palpation, i.e. the feel of tumor as opposed to that of normal tissue. To achieve operative success, however, it is necessary for the surgeon to somehow locate "occult" tumor, i.e. tumor which cannot be found by the conventional surgical procedures of sight and feel. Failure to locate and remove such occult tumor generally will result in the continued growth of cancer in the patient, a condition often referred to as "recurrent" cancer. In general, conventional diagnostic techniques such as, for example, use of the classic gamma camera and the like, fail to find or locate occult tumor. As tumor sites become smaller, the radionuclide concentrations at a given site will tend to be lost, from an imaging standpoint, in the background where blood pool radiation necessarily is present in the patient.

In 1984, Martin, M.D., and Thurston, Ph.D., introduced a much improved method for locating, differentiating, and removing neoplasms. Such technique uses a radiolabeled antibody and a portable radiation detection probe which the surgeon may use intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure now is known as radioimmunoguided surgery (RIGS®) (RIGS being a registered trademark of Neoprobe Corporation of Dublin, Ohio). The RIGS system for surgery additionally is successful because of a recognition that tumor detection should be delayed until the blood pool background of the circulating radiolabeled antibody has had an opportunity to be cleared from the body. As a consequence, the photon emissions or radiation emitted at minute tumors, compared to surrounding tissue, becomes detectable in view of the proximity of the probe device to it. Fortuitously, the radiolabeled antibody is capable of remaining bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand-held probe positioned in close proximity with the tissue under investigation. The seminal patent concerned with the RIGS procedure is U.S. Pat. No. 4,782,840 by Martin and Thurston, entitled "Method for Locating, Differentiating, and Removing Neoplasms," issued Nov. 8, 1988, and assigned in common herewith, the disclosure of which is expressly incorporated herein by reference.

The important advances achieved through radioimmunoguided-surgery have been reported. See in this regard, the following publications:

(1) "Radioimmunoguided Surgery System Improves Survival for Patients with Recurrent Colorectal Cancer" Bertsch, et al., *Surgery* 1995; 118: 634–639.

(2) "Radioimmunoguided Surgery in Primary Colorectal Carcinoma: An Intraoperative Prognostic Tool and Adjuvant to Traditional Staging," Arnold, et al., *American J. Surg.* 1995; 179: 315–318. localizing neoplastic tissue as part of this surgical procedure. ("Neoplastic tissue,"for the (3) "The Significance of Intraoperative Periportal Lymph Node Metastasis Identification in Patients with Colorectal Carcinoma," Schneebaum, et al., *Cancer* 1995; 75: 2809–2817.

(4) "Identification of Occult Micrometastases in Pericolic Lymph Nodes of Dukes' B Colorectal Cancer Patients Using Monoclonal Antibodies against Cytokeratin and CC49," Greenson, et al., *Cancer* 1994; 73: 563–569.

(5) "Intraoperative Detection of Occult Colon Cancer Micrometastases Using $^{125}I$-Radiolabeled Monoclonal Antibody CC49," Cote, et al., *Cancer* 1996; 77: 613–620.

The radioimmunoguided surgical system instrumentation is comprised generally of two basic components, a hand-held probe, as described above, which is in electrical communication via a flexible cable with a control console. This control console is located within the operating room facility but out of the sterile field, while the hand-held probe and forward portions of its associated cable are located within that field. The hand-held radiation detecting probe is relatively small and performs in conjunction with a cadmium-zinc-telluride detector or crystal.

The hand-held probe and preamplification electronics mounted within it in support of the cadmium-zinc-telluride crystal have been the subject of extensive scientific development. Cadmium-zinc-telluride crystals are somewhat fragile and exhibit piezoelectric properties which, without rigorous accommodation, will produce deleterious noise phenomena and the like. Further, the crystal and its operatively associated preamplification function are called upon to detect necessarily very faint radiation. In this regard, only a very small amount of radioactive locator will be associated with minute, occult tumor. Thus, radiation emission count rates measured with the RIGS system are relatively low. Research activity concerning the above operational criteria is reflected in the following U.S. Patents.

U.S. Pat. No. 4,801,803 by Denen, Thurston and Ramsey, entitled "Detector and Localizer for Low Energy Radiation Emissions," issued Jan. 31, 1989.

U.S. Pat. No. 4,893,013 by Denen, Thurston and Ramsey, entitled "Detector and Localizer for Low Energy Radiation Emissions," issued Jan. 9, 1990.

U.S. Pat. No. 5,070,878 by Denen, entitled "Detector and Localizer for Low Energy Radiation Emissions," issued Dec. 10, 1991.

U.S. Pat. No. 5,151,598 by Denen, entitled "Detector and Localizer for Low Energy Radiation Emissions," issued Sep. 29, 1992.

To derive data representing the presence or absence of occult tumor, a microprocessor-driven complex system of analysis continuously works to statistically evaluate validated counts or gamma strikes to aurally apprise the surgeon of the presence or absence of occult neoplastic tissue. One algorithm under which the noted evaluation takes place is described in U.S. Pat. No. 4,889,991 by Ramsey and Thurston, entitled "Gamma Radiation Detector with Enhanced Signal Treatment," issued Dec. 26, 1989.

The RIGS system, not only having demonstrated its value in locating occult neoplastic tissue, also substantially aids the surgeon in determining the proper staging of the patient in accordance with the extent and severity of the disease. Such staging aids in determining the appropriate post-surgical treatment of patients. In this regard, an effective staging technique utilizing the RIGS system has been described wherein an R Number is determined in accordance with the formula:

$$R\ Number = (n_1 \times E_1)_1 + (n_2 \times E_2)_2 + (n_3 \times E_3)_3 + (n_4 \times E_4)_4$$

wherein each subscript 1–4 represents an anatomic zone, staging of the patient being based upon the R Number determination. See generally, U.S. Pat. No. 5,482,040 by Martin, Jr., entitled "Biostaging of Adenocarcinomas Utilizing Radiolabeled Tumor-Associated Glycoprotein Antibodies," issued Jan. 9, 1996.

The RIGS system has been introduced into the field of laparoscopic surgery. See in this regard U.S. Pat. No. 5,429,133 by Thurston, et al., entitled: "Radiation Responsive Laparoscopic Instrument" issued Jul. 4, 1995 and U.S. Pat. No. 5,383,456 by Arnold and Thurston, entitled: "Radiation-Based Laparoscopic Method For Determining Treatment Modality" issued Jan. 24, 1995.

Cadmium telluride-based crystals, when employed in conjunction with the RIGS system perform admirably. Advantageously, higher purity levels for the compound crystals are not mandated in order to generate highly acceptable count-based outputs within an energy region of interest. Such performance, typically, is evaluated in conjunction with a multi-channel analyzer (MCA) relating counts with energy levels of interest. Where a sharp photopeak at the energy level of interest occurs which, in turn, is well spaced from regions of an MCA curve representing electrical noise, Compton scattering or the like, then windowing or thresholding out of such noise is a straightforward procedure. Cadmium telluride-based crystals achieve this excellent performance, inter alia, because they are used in conjunction with the radionuclide $^{125}$I which exhibits relatively low gamma energy (27–35 Kev). By contrast, the commonly employed $^{131}$I exhibits gamma energy of 360 Kev. The cadmium-zinc-telluride crystals employed with the RIGS system are, for the purposes of the instant discussion, considered to be "thin," i.e. having a thickness, d, of 2 mm. With the RIGS system, upon the occurrence of a photon event, a generation of carrier pairs generally will occur in a manner wherein holes are trapped at the grounded front face of the crystal. From that position they are immediately collected by the initial integration stage of a signal treatment system. The carrier electrons, traveling at a velocity which is about twelve times greater than the rate of hole migration, all move essentially the same distance, such that, even if they are trapped, they are trapped to the same degree, and the result is an excellently performing crystal detection system.

Over the recent past, practitioners have been desirous of utilizing instrumentation similar to the RIGS system in conjunction with higher energy radionuclides. In particular, a call has been made for a cadmium telluride-based hand-held probe device which is operable in conjunction with the use of the radionuclide Technetium 99-m. The latter radionuclide exhibits a gamma energy level of, for example, 140 Kev. That value is somewhat excessive for the cadmium-telluride crystal architecture employed with the RIGS system. However, utilization of a hand-held probe with higher energy nuclides for the purpose of lymph system tracking is achieving importance.

The involvement of the lymph system in tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is importantly involved in participation with the blood vascular system in developing the immune response of the lymphocytes and other cells. Lymph flows within the system as a consequence of a variety of perceived mechanisms of organ and tissue dynamics. For certain cancers, metastasis, occurring in consequence of lymph drainage, will result in an initial location or positioning of neoplastic cells at certain lymph nodes typically deemed "regional nodes" within a pertinent lymph drainage basin. Some cancers, for example, melanomas, have been observed to exhibit variability in lymphatic drainage patterns emanating from different portions of the body. Other cancers, such as those encountered in the breast, will evidence somewhat more predictable nodal involvement. In designing forms of cancer disease management, therefore, efforts are directed to the identification of affected lymph nodes. For melanomas, it has been a more recent practice to identify the pertinent drainage basin or regional nodes along with an evaluation of the extent of lymph involvement with micrometastasis. A presurgical step undertaken in about 20% of investigational procedures concerning melanomas looks to the carrying out of a gamma camera generated form of lymphoscintigraphy which gives the clinician a gross two-dimensionally limited image, generally showing the tumor site injection of sulfur colloid labeled with Technetium 99-m ($^{99m}$Tc) and, spaced therefrom, a region of radioactivity at the pertinent regional lymph nodes. The latter information at least confirms the path of drainage and the location of the proper drainage basin. Regional nodes then are removed and submitted for pathology evaluation.

For cancers, such as breast cancer, the sites of lymph node involvement are commonly encountered at axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics, as opposed to therapy. In this regard, the combination of the presence and extent of metastasis to the axilla represents the single most important prognostic factor for the management of patients with breast cancer. See generally "Cancer, Principles and Practice of Oncology," vol. 1, 4th ed., DeVita, Jr., el al., chapter 40, Harris, et al., J.P. Lippincott Co., Philadephia, Pa. (1993).

The axilla is a triangular region bounded by the axillary vein superiorly, the latissimus dorsi laterally, and the serratus anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by investment or fatty tissue and visualization of them necessarily is limited. Such dissection will pose risks of cutting the long thoracic nerve, the thoracic-dorsal nerve, the nerve to the pectorals major or the axillary vein. Morbidity may occur in some cases due to regional node removal, and patients are known to frequently discuss a numbing of the arm region following the procedure.

While this form of somewhat radical axillary lymph node dissection has been the conventional approach to determining nodal metastatic involvement, more recent data suggests that less radical axillary node evaluation procedures may generate equivalent information for staging and patient management, but with far more limited dissection and resultant trauma, as discussed below.

Patient management for staging purposes for the case of cutaneous melanoma is highly predicated upon determinations of lymph involvement. A number of factors are involved in the prognosis of the disease, including, inter alia, location, tumor thickness, level of invasion, growth patterns, and, of particular importance, the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial dialog has been carried on by investigators as to whether or not elective lymph node dissection, or lymphadenectomy, is an appropriate therapy. Elective lymphodenectomy has the major advantage of treating a nodal metastasis at a relatively early stage in its natural history when the tumor burden is low. On the other hand, such an approach may subject patients to surgery which would otherwise have been unnecessary. In particular, where patients exhibit a clinical Stage I level of the disease, there will be no nodal metastasis present, and no benefit then can be realized from regional lymphadenectomy.

Morton, et al., undertook an investigation of a procedure designed to identify that lymph node nearest the site of a melanoma and within the pertinent lymph drainage basin. Such a node, being on the most direct drainage pathway will present the most likely site of early metastasis and is referred to as the "sentinel node." Thus, by carrying out only a limited dissection, specific to this node and performing pathologic analysis of it, staging can be achieved without at least initial resort to more radical lymphadenectomy. With the approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively of blue color and readily identified. Thus, the sentinel draining lymph node of each primary melanoma is isolated and removed. By examining the sentinel nodes, for example by frozen section using routine hematoxylin-eosin histopathological techniques, as well as rapid immunohistochemical techniques, only those patients who have evidence of micrometastasis in the sentinel draining node are subject to subsequent lymphodenectomy. See generally, Morton D., Wen D-R, Wong J., et at. "Technical Details of Intraoperative Lymphatic Mapping for Early Stage Melanoma," *Arch. Surg.* 1992: 127:392–399; and R. F. Uren, et. al, "Lymphoscintigraphy in High-Risk Melanoma of the Trunk: Predicting Draining Node Groups, Defining Lymphatic Channels and Locating the Sentinel Node," *J. Nucl Med* 1993; 34:1435–1440.

The approach of Morton, et al., also has been undertaken to moderate the otherwise somewhat radical axillary lymph node dissection common in staging breast cancer. Through the utilization of the noted vital dyes, in conjunction with the lymph drainage system from primary breast tumor, less radical sentinel node based procedures may result in adequate axillary staging and regional control. With the procedure, in general, a vital blue dye is injected into the breast mass and surrounding breast parenchyma. Following a relatively short interval, a transverse incision is made just below the hair bearing region of the axilla. Blunt dissection is performed until a lymphatic tract or duct leading to a blue stained node is identified. The lymph duct, having a blue color, provides a guide path leading to the location of the most proximal lymph node and thus the sentinel node. This sentinel node is excised and evaluated. While the procedure calls for considerable surgical experience and talent associated with the delicate task of following the blue duct (a ruptured dye-carrying duct can be problematic), the ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes. See generally Guiliano, A. E.; Kirgan, B. M.; Guenther, J. M.; and Morton, D. L., "Lymphatic Mapping and Sentinel Lymphadenectomy for Breast Cancer," *Annals of Surgery*, vol. 220, no. 3: 391–401, 1994, J.B. Lippincott Company.

As a replacement for or an adjunct to the tracking of portions of the lymph system to locate a sentinel lymph node, practitioners have injected the noted sulfur colloid labeled with $^{99m}$Tc technician at the site of the lesion. Then, employing a hand-held radiation detecting probe, migration of the injectate along the lymph ducts to the sentinel node is carried out. Thurston, et al, in U.S. Pat. No. 5,732,704 entitled "Radiation Based Method for Locating and Differentiating Sentinel Nodes," issued Mar. 31, 1998, describe an improved technique for thus tracking a lymph duct and for utilizing a thresholding procedure three-dimensionally finding a radiolabeled sentinel lymph node with a hand-held probe.

As the use of radionuclides in the course of diagnostics and management of disease has expanded significantly over the past two decades, a concomitant need has arisen for instrumentation exhibiting a flexibility of use. Higher levels of computing power now are called for along with a flexibility or adaptability of performance. This calls for software driven equipment with software restructuring capabilities so as to readily convert equipment to new procedures and techniques which may employ a wide range of different radionuclides. Equipment improvements facilitating readout values and enhanced surgical data reporting are needed by practitioners both to ease the burden necessarily imposed within the surgical theatre and to evoke higher levels of measurement accuracy.

BRIEF SUMMARY OF THE INVENTION

The present invention is addressed to a system and apparatus for detecting radiation emanating from a radionuclide-based source having predetermined gamma energy levels. The system includes a control assembly incorporating interactive controls and display design to more efficiently respond to command inputs from the practitioner and to provide more readily perceived visual readouts. Capable of performance with a variety of radionuclides, the system particularly is configured for operating at either a RIGS or an ILM mode in response to actuation of a mode selection switch.

The console housing system includes a relatively large window display providing not only brightly illuminated count rate information, but an icon-based imagery, identifying not only the operational features to which the published count rates apply but also, through the use of intermittent energization or flashing, apprises the operator that a count measuring function is underway. In this regard, a target icon flashes during the interval occurring during a target check or a target count activity. Normally, a background icon flashes during the interval occurring during a background count.

The target count and target check values are displayed for a limited interval of five seconds. In the former regard, the system computes a target count to background count ratio and displays that ratio value for the same limited interval in conjunction with a ratio icon. To further apprise the practitioner of the time remaining to conclude a target or background data collection procedure, a multi-segmented bar graph is provided at the display which fills from first to last segment in accordance with the time elapsed for the procedure.

Performance of the system is facilitated by an automated selection of both probe detector bias voltage values as well as energy window reference values in correspondence with an elected radionuclide. Windowing performance at higher frequency pulse rates is improved with the incorporation of a time-dependent base line restoration network.

Noise avoidance is enhanced within the system through the incorporation of a discriminator circuit which evaluates not only energy window-based signals, but also evaluates the width of each pulse with respect to a maximum pulse width duration corresponding with noise. Where the surgeon wishes to avoid the aural output of the system, a mute switch is provided which blocks such outputs while maintaining a "beep" feature as an aural feedback for switch actuation.

Other objects of the invention will, in part, be obvious and will, in part, appear hereinafter. The invention, accordingly, comprises the system and apparatus possessing the construction, combination of elements and arrangement of parts which are exemplified in the following detail description.

For a fuller understanding of the nature and objects of the invention, reference should be made to the following detail description taken in connection with the accompanying drawings.

BRIEF DESCRIPTION OF THE DRAWINGS

FIGS. 5A–5D combine as labeled thereon to provide a block diagram of the control system employed with the console shown in FIG. 1;

FIGS. 8A–8C combine as labeled thereon to provide a flow chart describing the main program utilized by a central processor control of the console shown in FIG. 1.

DETAILED DESCRIPTION OF THE INVENTION

Figure 1:
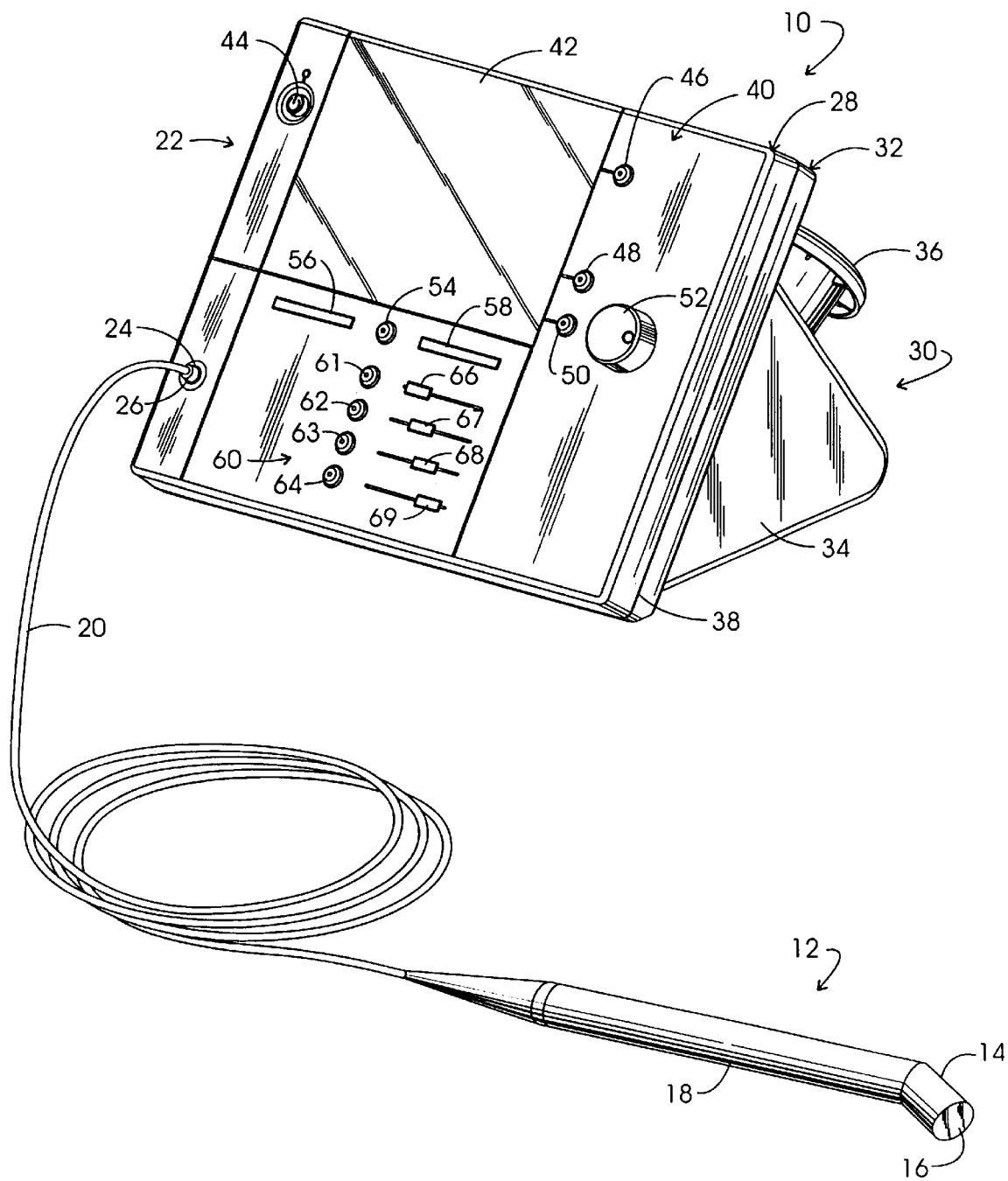
FIG. 1 is a perspective view of a system according to the invention including a console and associated hand-held probe.

Referring to FIG. 1, the system of the invention is represented generally at 10. System 10 performs in conjunction with a hand-held radiation detecting probe represented generally at 12. Probes as at 12 are selected to perform in conjunction with any of a number of medical procedures and, thus, may assume a variety of configurations. Predominating for the present purposes, however, the probe 12 will perform in conjunction with radioimmunoguided surgery procedures (RIGS) wherein a cadmium telluride crystal based detector performs in conjunction with a systemically injected locator which, for example, may be an antibody labeled with the radionuclide $^{125}I$. That procedure may utilize probes having a general structure as shown at 12 or probes intended for laparoscopic surveys or investigations. Another predominant use of the hand-held probes is involved with intraoperative lymphatic mapping (ILM). ILM procedures generally employ a higher energy radionuclide such as $^{99m}Tc$ which is injected at the sitis of a lesion and the probes then are utilized to locate that node within a lymph drainage basin designated as a "sentinel" node. Probes as at 12 may assume a variety of configurations. In this regard where cadmium telluride crystal detectors are employed, then different operational modes for these crystals are utilized based upon the radionuclide energy involved. In general, probes as at 12, will incorporate a forward structure as at 14 containing a crystal mount for retaining a detector crystal such as cadmium telluride. The forward face of such crystal typically will be in very close proximity but spaced from a radiation transmissive window as at 16. Extending rearwardly from the forward structure 14 is a hand-grippable handle portion 18 which may support signal treatment circuitry such as preamplifiers and the like. A pulsed output is generated from this preamplification function in response to photon events or interactions with the detector crystal and such pulsed outputs are conveyed, typically, by a flexible cable or suitable transmission assembly as at 20 to a control assembly represented generally at 22. In this regard, a connector 24 at the outward end of flexible cable 20 is connected in electrical association with the corresponding connector 26 of the assembly 22.

Control assembly 22 is seen to be formed having a forward housing component 28 of generally rectangular peripheral design. Forward component 28 is joined with a rear housing component represented generally at 30. This component 30 includes a rectangular forward support portion 32 which meet with the rearward edge of forward housing component 28. Additionally, the rear housing component 30 includes a rearward support portion 34 having a somewhat triangular cross section and which is integrally molded with the forward support portion 32. This provides for the support the forward housing component 28 at a convenient, rearwardly tilted orientation as shown. Preferably, the amount of such tilt is about 57°. This angularity facilitates manual switch actuation and adjustment by the user as well as promotes the readability of a readout display. Inasmuch as the control assembly 22 is powered from a conventional A.C. line voltage source, a cord wrap fixture 36 is molded within the rearward support portion 34. In general, the forward housing component 28 and rear housing component 30 are injection molded of an ABS/Polycarbonate blend which is resistant to the solvents and disinfectants typically encountered in the medical field. It may be noted that a parting line or joint 38 is present at the juncture or union of forward housing component 28 and the rectangular forward support portion 32 of rear housing component 30.

The forward face of the control assembly 22 is represented generally at 40 and is seen to support a relatively large readout main display window 42. Window 42 is formed of a polycarbonate that will make a strong weld joint with the ABS/Polycarbonate forward housing component 28. The view through the display window 42 is enhanced by an antiglare coating and an ultraviolet cured coating is employed with the window 42 to improve its scratch resistance. All front housing transparent components are ultrasonically welded in place to assure that liquids will not breach the enclosure. Between the window 42 and the forward housing component 28 is a graphics overlay which contains informational symbols and functions to provide organization to multi-segmented character forming light emitting diodes (LEDs) mounted just rearwardly of the forward face 40, including window 42. Such LEDs serve to provide a very bright and readily discerned visual readout of readily perceived by the surgeon working at the somewhat remote sterile field of a surgical theatre.

The most predominately utilized manual control components are mounted at the forward face 40 of the control assembly 22. In this regard, where switches are employed, they are formed of a silastic button style configuration, for example a material sold under the trade designation "Santoprene" marketed by Scientific Molding Corp., of Somerset, Wis. Looking to the switch assemblies, an on/off switch is provided at 44 at one side of the display window 42. Adjacent the opposite side of display window 42 is a "target" switch 46. When the momentary on target switch 46 is pressed and immediately released, a "target check" procedure representing a two second count by the probe 12 is carried out. Where the switch 46 is held on or actuated for at least one second, a "target count" procedure is carried out for an interval of six seconds. These latter count intervals are exclusive to the operation of system 10 in a RIGS mode. Next below the switch 46 is a background count switch 48. Switch 48 is used in a RIGS mode of operation for the development of statistically significant thresholds, counting for background occurring utilizing probe 12 at a predetermined location during and just prior to surgery. Next below the background count switch 48 is a mute switch 50. During some procedures, the practitioner will wish to avoid the audio output of the system with the exception of aural feedbacks for switch actuation. Accordingly, those former sounds may be muted by actuating switch 50 which will perform in all operational modes including RIGS and ILM. The level of audio output is controlled by a volume encoder shown as a knob 52. Encoder 52 provides a coded input of from one to 128 positions such that control software can provide a broad variety of audio output volumes depending upon the mode employed with the system 10.

Below the center of display window 42 is a mode selection switch 54. Actuation of switch 54 alternately elects the two predomninate operational modes of system 10, i.e., a RIGS procedure which will result in the illumination of an elongate rectangular output display at 56. This RIGS mode of operation additionally is referred to as "binary pitch" operation. Alternate actuation of switch 54 will elect an ILM operational mode with the illumination of an elongate rectangular output display 58. The latter mode of operation also is referred to as a "dynamic pitch" operation. For the latter operational mode, in view of the high energy level and larger quantities of radionuclide material employed, count rate ranges may be elected by the operator. Accordingly, an array of range switches represented generally at 60 are mounted at the forward face 40. The momentary push switches are shown at 61–64 and respectively correspond with ranges of 0–100 CPS, 0–1000 CPS, 0–10000 CPS, and 0–50000 CPS. With the election of a given range by actuation of one of the switches 61–64, a corresponding range indicator shown respectively at 66–69 is illuminated. In general, each of the ranges will incorporate an initial threshold level below which no audible or visual cueing will occur. That range, for example, may be 2% of the maximum count value for the given range. The ranges also may be restricted by a background count initiated at switch 48.

Figure 2:
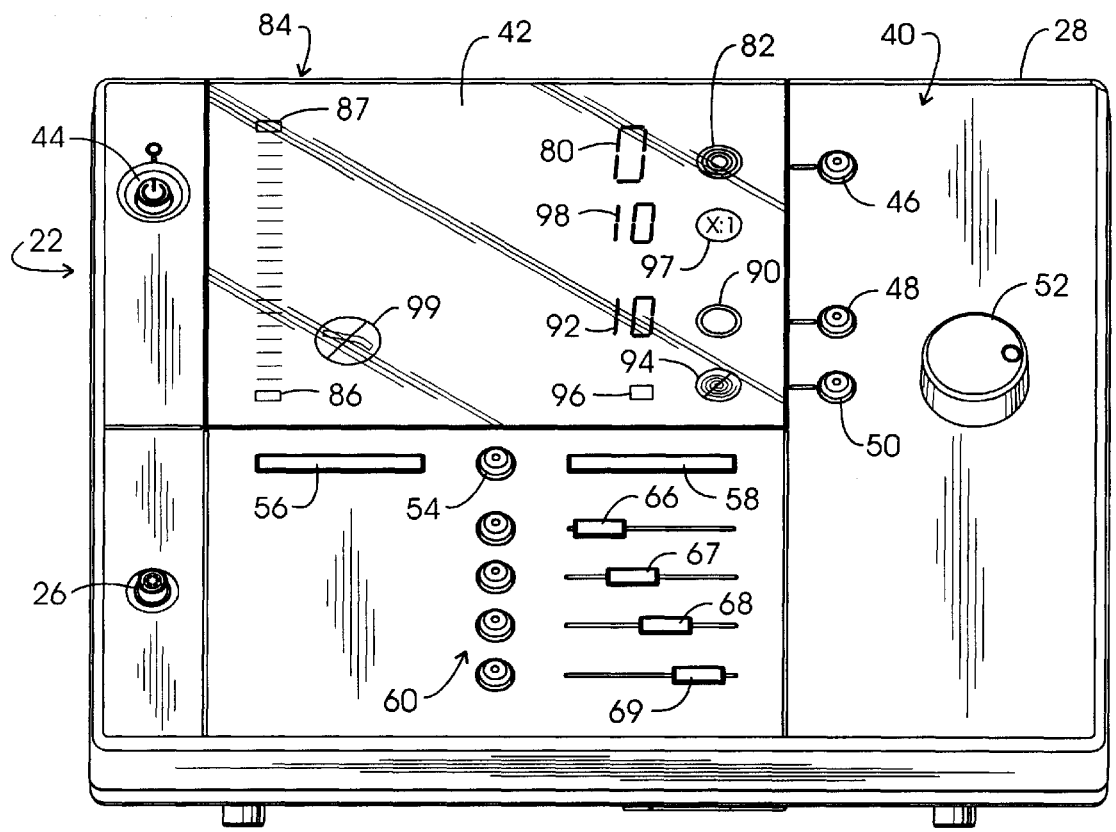
FIG. 2 is a front view of the console shown in FIG. 1.

Referring to FIG. 2, the forward housing component 28 again is revealed. However, shown at the display window 42 are visual readouts which are generated in conjunction with the operation of system 10. To facilitate the ease of operation of the system 10, on a worldwide basis, icon imagery or graphical labels are employed, inter alia, in conjunction with the switches 46, 48 and 50. Colors also are used to indicate relationships between data items and to enhance understanding of the displays. Further, the visual indicators have the ability to be flashed or energized intermittently in order to draw attention to a given data or procedural item. The indicators also are operated in a manner to help differentiate between a period when the data item is being acquired by system 10 and the period when the acquired data then is being displayed. In this regard, a flashing indicator generally means that the associated data item is being updated as a result of an operator action.

Running count rate data is published at the window 42 with a large bright LED derived segmented character representation which is located generally horizontally from the target switch 46. This numeric readout is shown at 80 in FIG. 2. During the operation of the system 10 when the target counts are not underway in consequence of the actuation of switch 46, the count rate data published at 80 is updated each ½ second. However, where the practitioner actuates the target switch 46 for example, in a RIGS mode of operation to derive a target check, then the numeric data at 80 disappears in favor of dashes and an icon assembly containing an icon 82 with the shape of an international target is intermittently energized or flashed for the two second collection period. This same flashing occurs in conjunction for example, with the six second target count data collection occurring during the RIGS mode of operation. Following the data collection interval, then the target count or target check count rate information is published utilizing the numeric output 80 and is sustained at the window 42 for the relatively short display interval, for example of five seconds. Following that display interval, then the conventional ½ second updated count rate data is published in conjunction with the readout indicia as at 80. At the opposite side of the display window 42 there is provided a sixteen segment bar graph represented in general at 84 and having bottom and top (first and last) illuminated segments shown respectively at 86 and 87. To apprise the practitioner of the amount of time remaining for the collection of data associated with the actuation of target switch 46, the LED implemented sixteen segment bar graph 84 will "fill" or illuminate segment by segment from bottom segment 86 toward top segment 87 during the predetermined data collection intervals. Thus, the surgeon will be aware of how much additional time the probe 12 should be retained in count position. When the system is operated in an ILM mode, this same form of information is provided, however, it is tempered or improved with respect to a number of data points collected representing an adequate degree of confidence. This follows, for example, in the ILM mode because of the relatively larger count rates involved, permitting a rapid development of confidence levels. Thus, with the exception of lower and upper bounds in data collection times, at higher count rates the segments of the bar graph 84 will fill for this ILM procedure on an expedited basis.

Actuation of the background switch 48 while system 10 is in a RIGS mode will cause the carrying out of a six second background count evaluation. During the progress of this background counting, a background icon assembly 90 represented as a dual ring is energized on an intermittent or flashing basis. While the six second counting ensues, the bar graph 84 will correspondingly "fill" from lower segment 86 to upper segment 87 in correspondence with that set six seconds. The background value will be published as numerical indicia as at 92 at the termination of the interval. With the completion of background computation, the system 10 will compute a ratio of background count rate to the currently measured count rate and publish it as at 98 along with a ratio indicia (97) intermediate icons 82 and 96 and indicia 80 and 92. During the ILM mode, the bar graph 84 publishes count rates over the earlier noted default threshold or, when utilized, over a background count ratio, the segments of the bar graph 84 are energized from first to last in accordance with the difference between either threshold or background and the current level of count. Such display also reflects the range selected from the switch array 60. The audio output of the system 10 when operating in the noted ILM mode, also provides a varying pitch or frequency output which is compressed between the lower threshold or background count and the upper frequency limit.

Actuating the mute switch 50 in the course of a procedure provides for the energization of a mute icon assembly represented at 94. The icon 94 so displayed represents a sound wave pattern with a slash positioned across it. Also illuminated during the course of a procedure at one of six rectangular positions across the bottom of display window 42 is an illuminated indication of the type of radionuclide utilized. The ILM mode indicator, depicting $^{99m}$Tc, is shown in FIG. 2 at 96. The system 10 defaults to this indicator upon actuation of switch 54 for one mode. Correspondingly, another actuation of mode switch 54 will illuminate a similar indicator at the opposite side of window 42 showing a $^{125}$I radionuclide utilization. Four other radionuclides may be selected with the system by actuation of a switch (not shown) mounted at the rear housing component 30 (FIG. 1). Radionuclides which may be elected are, for example: $^{57}$Co, $^{111}$In, $^{18}$F and $^{131}$I and at such time as the system 10 is activated, but probe 12 is not connected properly or inoperative, a probe defect icon as at 99 is energized at the lower left side of display window 42.

The software driven control features of system 10 perform in conjunction with a standard bus architecture referred to as "PC/104". This standard bus approach is desirable in view of a small form factor (3.55 inch by 3.25 inch) which reduces crowding within the control assembly 22 enclosure. Control architecture including a CPU board, an I/O board, a DSP board and a unique pulse detector module (PDM) are mounted to the PC/104 mother board or backplane and are located outwardly from but parallel therewith. The forwardly directed surface of this backplane functions, inter alia, to support the LED based circuits associated with display 42, as well as the range displays 66–69 and the mode selector displays 56 and 58. That face of the board also cooperates with the manually actuated components of the switches at forward face 40.

Figure 3:
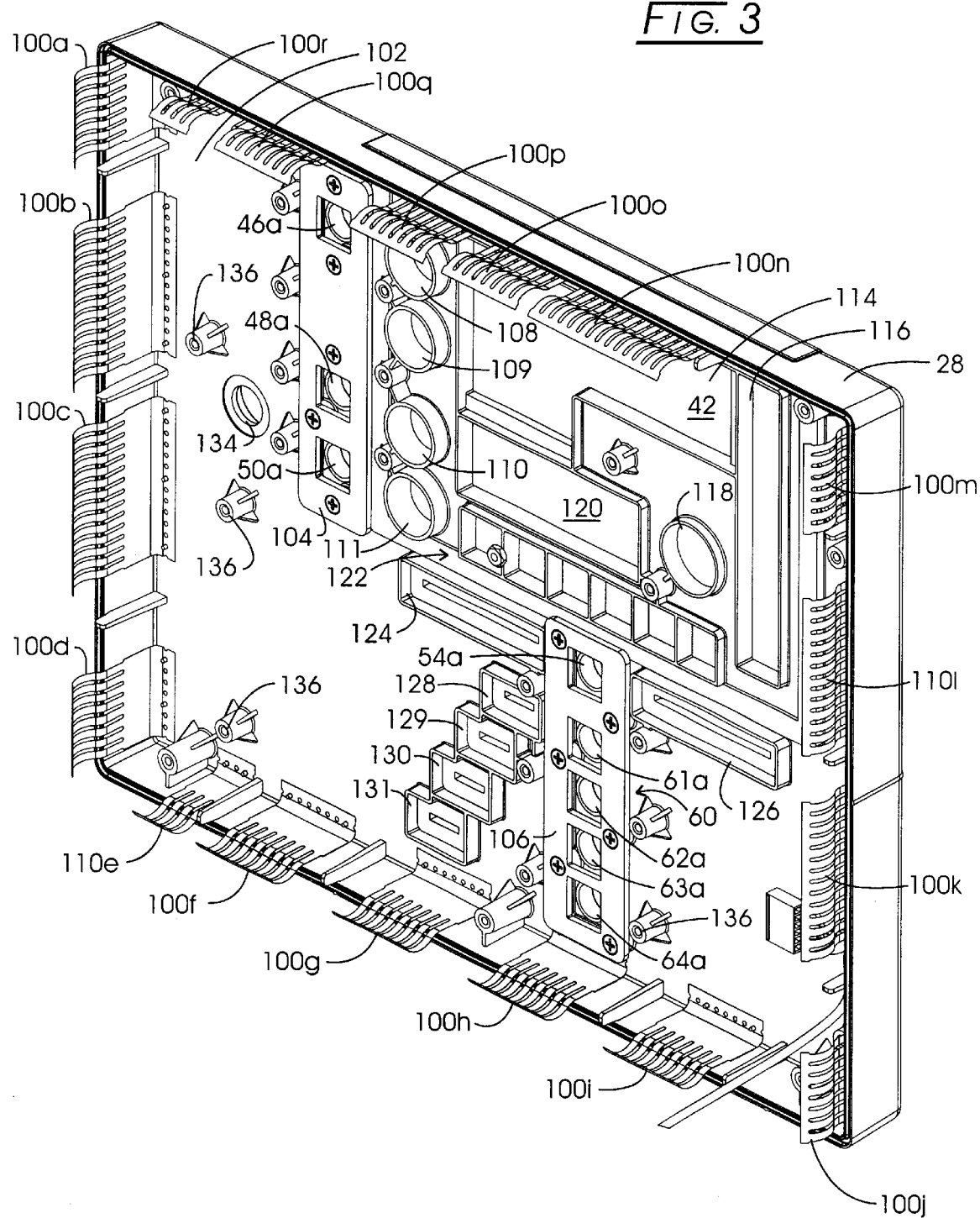
FIG. 3 is a perspective view looking into the internal side of a forward housing component of the console shown in FIG. 1.

Looking to FIG. 3, the rearward side of forward housing component 28 is revealed as it appears before the positioning of the noted backplane and its associated and supported components. In FIG. 3, a tongue-in-groove form of edge connection as described in FIG. 1 at parting line 38 is revealed with the same numeration. To provide for EMI filtering, the entire interior surfaces of both the forward housing component 28 and rear housing component 30 are coated with an aluminum containing conductive material which is vacuum deposited. To preserve the integrity of the shield at the union between components 28 and 30 as at parting line 38, the interior surface of forward housing component 28 supports a plurality of EMI gaskets 100a–100r formed, for example, of beryllium-copper spring like material. When the forward housing component 28 is mated with rear forward support portion 32 of rear housing 30, the gaskets 100a–100r complete the EMI security feature. Switches 46, 48 and 50 are formed having silastic cup-shaped cover assemblies which extend through openings within the forward face 40. As they extend through that forward face, the outwardly flared inward edges of these switch covers are compressibly retained against the rear surface 102 of forward housing component 28. To secure them in this compressed arrangement, a metal switch-plate 104 is secured against them using machine screws. In similar fashion, cup-shaped silastic switch cover assemblies 54a and 61a–64a are retained at the back surface 102 by a metal switch-plate 106. In general, when the practitioner depresses one of the elastomeric cup-shaped switch cover assemblies, contact is made with corresponding conductive switching elements which are supported upon the forward face of the noted backplane. The minimization of discrete wiring thus achieved is a substantial advantage in fabrication of the control apparatus 22.

To avoid cross talk or light scatter, for the most part, the LED illuminated display features including icons, indicators and numerical indicia as well as bar graph 84 are formed as assemblies with baffles isolating the light emitting components. In this regard, the circular icons including target icon 82, the ratio icon (97) background icon 96 and mute icon 94 are retained within respective light restricting cylindrical baffle channels or wells 108–111. In similar fashion, the numerical indicia representing general count rate as at 80 and the ratio valuation 98 just below it are retained within a rectangularly shaped light restricting channel 114. Adjacent to light restricting channel or baffle 114 is another vertically oriented rectangular light restricting channel 116 at which the multi-segment bar graph 84 is located. Adjacent to channel 116 is another light restricting cylindrical baffle or well 118 which surrounds an LED array functioning to illuminate icon 99 representing that probe 12 is inoperative. Below the light restricting channel 114 and baffle 118 is another rectangular light restricting channel 120 which is employed with background count rate numerical indicia published by LED formations mounted upon the noted backplane. Next below the channel 120 is a horizontal sequence of six light restricting channels or baffles of generally square configuration which function to confine light extending to a display showing the earlier noted radionuclide identifications including, for example, that for $^{99m}$Tc shown at 96 in FIG. 2. This array is represented generally at 122. Below the array of light restrictors 122 are two elongate rectangular light baffle channels 124 and 126 which surround LED illuminator arrays providing the mode indicator illumination described at 58 and 56 in FIG. 2. Next extending below the channel 124 is a sequence of four rectangular channels 128–131 which baffle and confine light from light emitting diode arrays serving to illuminate the respective range indicators 66–69 described in FIG. 2. Access for the volume encoder knob 52 as seen in FIG. 2 is provided through an opening 134 which, as with all the above described components cooperates with the backplane. Additionally shown on the drawing are a plurality of standoffs, some of which are identified at 136 which are employed for purposes of securing the backplane or mother board to this forward housing component 28.

Figure 4:
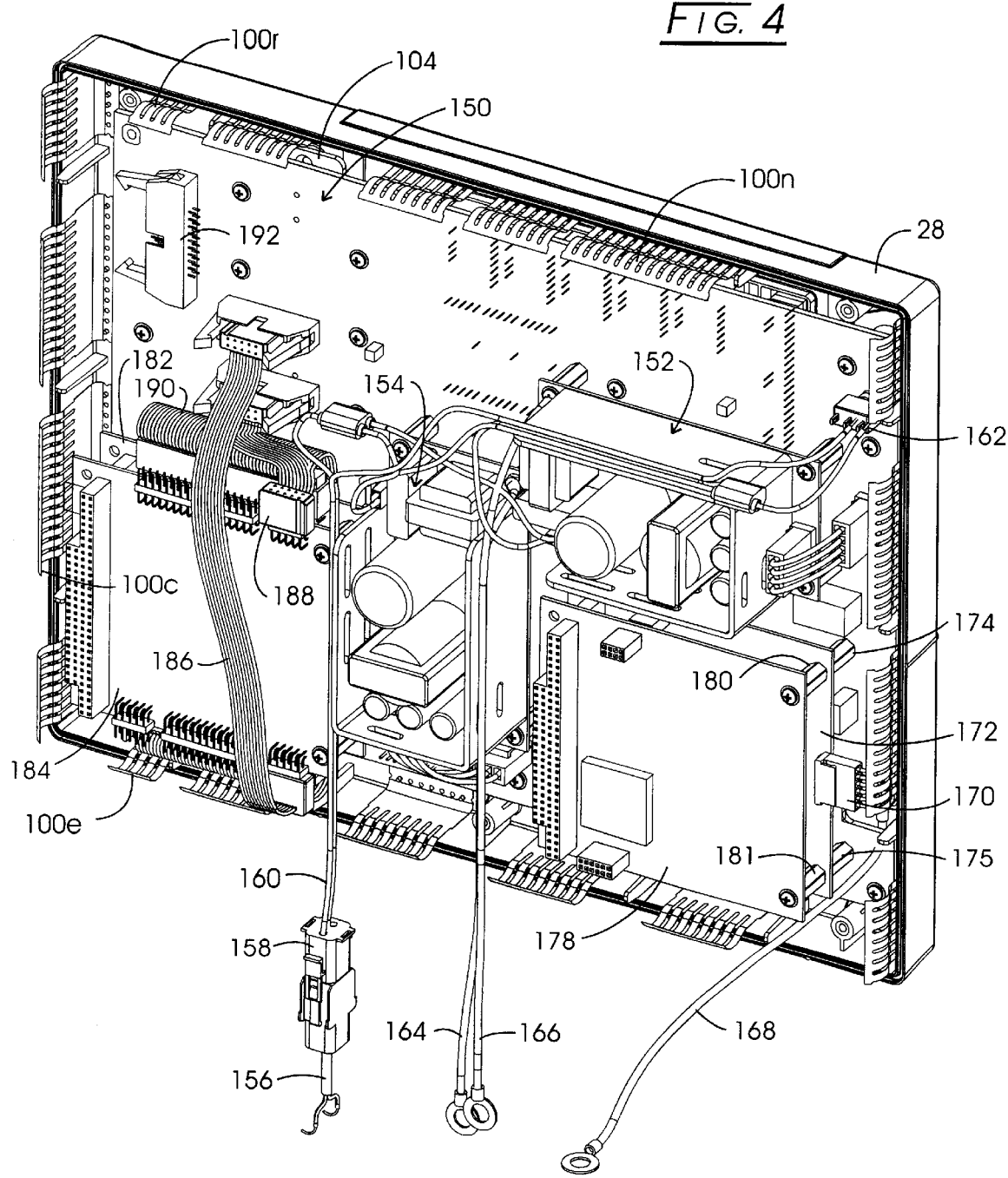
FIG. 4 is a perspective view of the forward housing component of FIG. 3 with the inclusion of power supplies and circuit boards.

Turning to FIG. 4, the forward housing component 28 again is shown but with the installation of the noted backplane with standard PC/104 bus and associated backplane mounted components. In the figure, the backplane is represented in general at 150 and is seen to have a thin rectangular structural aspect dimensioned to be positioned against the rearward structure of component 28 as described in connection with FIG. 3. Mounted upon the rearward face of backplane 150 is a generally horizontally disposed open-framed 12 volt power supply represented generally at 152, and vertically oriented in adjacency therewith is a 5 volt open-framed power supply represented generally at 154. Each of these power supplies are electrically connected with an a.c. utility input introduced from the rear housing component 30 (FIG. 1). That a.c. input is directed via a cable seen in FIG. 4 at 156 which extends through an a.c. line filter 158 and thence, as represented at 160 to power supplies 152 and 154. Additionally coupled with this input and power supply circuit is the power, on/off switch 44 terminal at 162 which is supported on the backplane 150.

Positioned in parallel stacked relationship and in electrical communication with the bus architecture of the backplane 150 are four rectangularly shaped circuit boards. As before, by being associated with this standardized bus structure, substantial amounts of lead connections are eliminated and the more ideal data transfer interconnections of a bus system are realized. Further, such structuring provides independent upgradability of each circuit board under the PC/104 standards criteria. Power converter grounds are provided from the rear of the assembly 22 from flexible cables as seen at 164 and 166, while in similar fashion, probe 12 ground input is provided from the rearward component 30 of assembly 22 by a flexible cable connection as represented at 168. This connection 168 extends to a probe dedicated terminal 170 which, in turn, is electrically associated with the input connector 26 (FIG. 1). Terminal 170 is seen in electrical connection with a printed circuit board 172 upon which is formed a signal treatment circuit. In this regard, the board is generally referred to as a pulse detector module board (PDM). Mounted to the rearward face of backplane 150 by standoffs, two of which are revealed at 174, 175 and multiple pin connectors (not shown) the signal treatment carried out at the board 172 is one treating the pulse output from a preamplification stage contained within the probe 12 itself. Connected within the bus architecture and parallel adjacency with PDM board 172 is a printed circuit board 178. As before, mechanical connection is made utilizing standoffs, two of which are seen at 180 and 181 and multiple pin connectors. Board 178 supports a digital signal processor circuit (DSP) The DSP component utilized with board 178 is a type TMS 320 series by Texas Instruments, Inc. of Dallas, Tex., and the board employing that DSP is a Starburst type 104C31 marketed by Nova, Inc., of Cincinnati, Ohio. On the opposite side of the 5 volt power supply 154, there is provided an input/output circuit board 182 which provides a 48 line I/O function performing in conjunction with the standardized bus architecture. The board 182 may be provided, for example, as a part number EMM-DIO-PO by Diamond Systems, Inc., of Polo Alto, Calif. Mounted over and in parallel adjacency with the board 182 is a central processing unit board 184 (CPU). The CPU board 184 may be provided, for example, as a model 4 DXi marketed by Ampro, Inc., of San Jose, Calif. The CPU function at board 184 is a 133 MHz 486DX based PC/104 board with onboard programming of flash memory, floppy/IDE interface, serial ports, parallel port and serial boot loader capability. Software and onboard programming capabilities enables the software of system 10 to be upgraded without removing board 184 from the control assembly 22. Cables associated with the CPU function at board 184 are seen at 186 and 188 while I/O cable is seen at 190. Not shown in the figure but mounted for access at the rear housing component 30 is an axillary board carrying a manually actuable switch for selecting any of the earlier six noted radionuclide mode setups. Additionally, a data (serial) port is provided which is electrically associated with the central processor control at board 184. Further included but not shown in the drawing is a cooling fan mounted at rear housing component 30. A connector is shown at 192 mounted upon backplane 150. It may be used in conjunction with the noted auxiliary board.

Figure 5A:
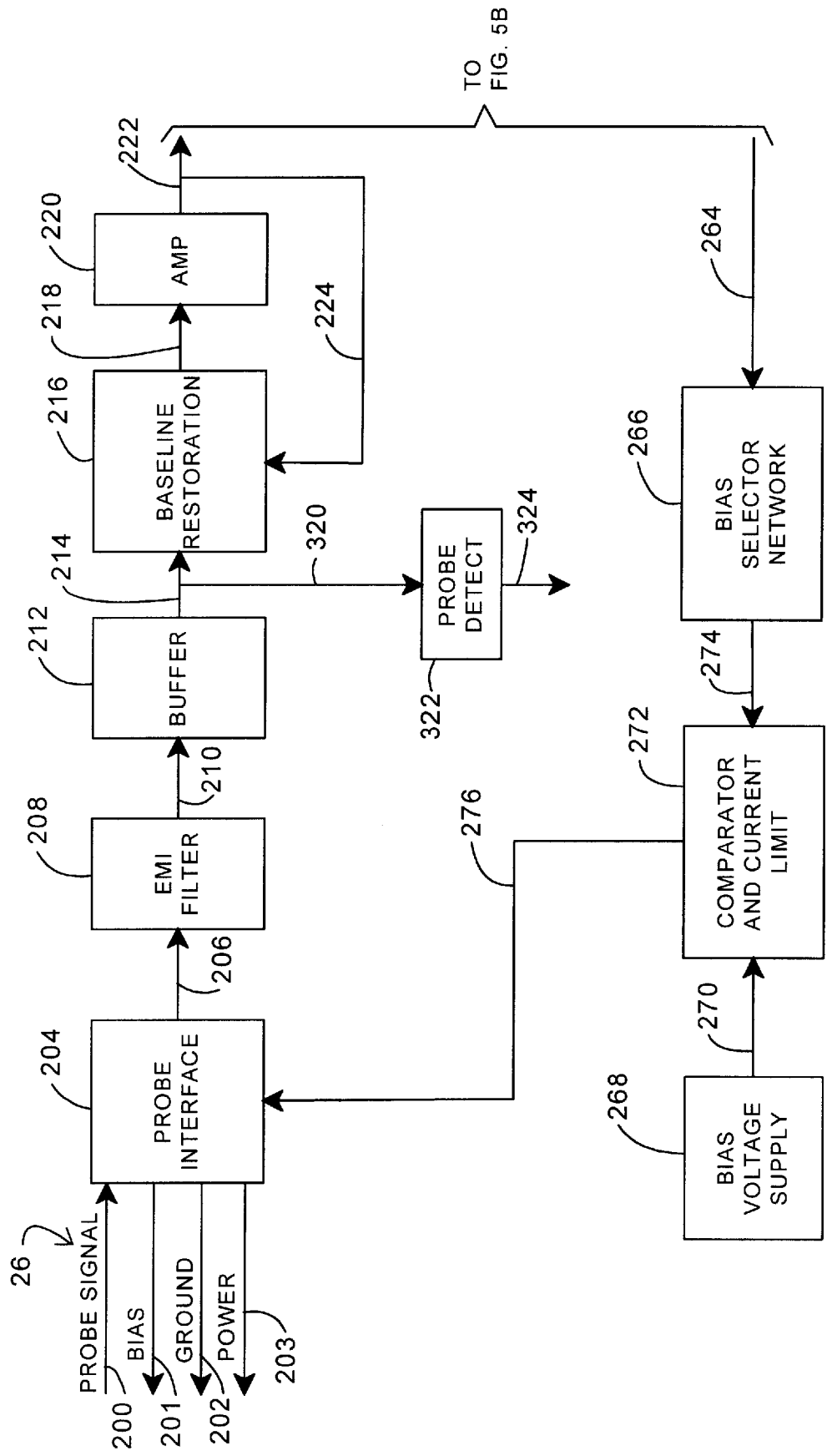

FIGS. 5A–5D are block diagrammatic representation of the control system. These FIGS. 5A–5D should be considered in an orientation established by the labeling thereon. Referring to FIG. 5A, connector 26 is represented in general as looking to four components of the interface of control apparatus 22 with the probe 12. In this regard, as represented at line 200, a data signal present as a pulsed output will be carried by a line represented at 200. From the control circuitry, a voltage bias is provided at line 201 for the operation of the detector component of the probe 12. Similarly, ground as represented at line 202 is carried to the probe 12 detector component and, as represented at line 203, circuit power, for example at +12 volts is supplied to the probe 12. Lines 200–203 are shown in operative association with a probe interface circuit function represented at block 204. The pulsed output as provided at line 200 generally will exhibit a narrowness which in terms of time will be of two to seven microsecond duration at 10% of its height. From the interface function 204, the pulse signal or pulse train is introduced, as represented at arrow 206 to an EMI filter network represented at 208. Stage 208 functions to remove very high frequency EMI noise and has no operational effect upon the pulsed output. From the filtering function 208, as represented at arrow 210 and block 212, the pulsed output is buffered. In general, the buffer stage 212 is implemented as a unity gain operational amplifier. The thus buffered signal, as represented at arrow 214, then is submitted to a baseline restoration network represented at block 216. In general, the function at block 216 is one incorporating an a.c. coupling capacitor. At very high pulse rates, without baseline correction, the resultant pulse train tends to degrade, falling below the lower threshold of a window circuit which is later encountered. To correct for this phenomenon, a time-dependent base line restoration network is provided which derives a soft clamp retaining the output of the coupling capacitor at, for example, ground in the absence of a pulse. This avoids the noted downward drift of the pulse train. The advantage of this form of baseline restoration resides in its immunity to any distortion of pulse height. Thus, probes of different operational pulse widths can be employed with the system. From the baseline restoration at block 216, as represented at arrow 218 and block 220, the signal then is amplified. The amplification stage represented at block 220 is one, for example, providing a gain of 2.5. The resultant amplified signal then is present at arrow 222. That output is tapped as represented at arrow 224 to provide the noted time dependent input to the baseline restoration network 216.

Looking additionally to FIG. 5B, arrow 222 reappears as it directs the amplified probe signal to a validation network including upper limit and lower threshold energy comparators as represented at block 226. The network 226 identifies those pulses which are above a lower threshold reference which, for convenience, is provided at ground and which exceed a reference level representing an upper limit. The resulting data then is presented, as represented at arrow 228, to an energy and pulse width discriminator function represented at block 230. In general, the function 230 is implemented with a programmable logic device (PLD). This logic device validates the pulses which are below the upper limit and above the lower threshold of the window function represented at block 226. Additionally, the function at block 230 times the pulse identification at the lower threshold of the window comparator function at block 226 to determine pulse width. Experience with the system 10 has shown that valid pulses will exhibit a pulse width at that lower threshold of less than about 12 microseconds. Lengthier pulse widths statistically will represent noise. Thus, a logical ANDing activity occurs at the function 230 requiring pulse validation with respect to the windowing function represented at block 226 and with respect to pulse width as evaluated from the lower threshold comparator of the windowing network. The PLD device implementing function 230 performs under the supervision of a central processor control or central processing unit (CPU) as represented at block 232 and arrow 234.

Upon being validated, a pulsed output then is transferred to a digital signal processing activity (DSP) as represented by arrow 236 and block 238. This DSP network has been described in conjunction with DSP circuit board 178 in FIG. 4. The DSP function 238 is slaved to or controlled by the central processor control 232 as represented at arrow 240 and provides signal information thereto as represented at arrow 242. Data transfer with respect to the PC/104 bus architecture between the DSP function at block 238 and the central processing function at block 232 is represented by the bus arrow 244. In general, the DSP function 238 develops count rate data in accordance with a variety of algorithms which additionally determine the statistical significance of count rates with respect to background count rate and the generation of count rate data which is displayed at display window 42.

As represented by arrow 246 and block 248, the central processor function 232 also develops an analog reference voltage level which is employed to provide the reference level for the upper limit and lower threshold comparators at the window function represented at block 226. A digital-to-analog function which is made available at the DSP board function represented at block 238 is utilized for this purpose. By providing a control over the analog reference level from the central processor and DSP 238, that processor can react to the selection of a particular radionuclide by the user and automatically apply the proper window references. In this regard, the analog output from the function represented at block 248 is directed as represented at arrow 250 to a reference ranging network represented at block 252. The ranging function at block 252 asserts a precision with respect to the applied analog reference level by performance with a precision reference voltage developed at the PDM circuit board 172 described in conjunction with FIG. 4. The appropriately perfected references then are supplied to the upper and lower energy window comparators as represented by arrow 254.

Figure 5C:
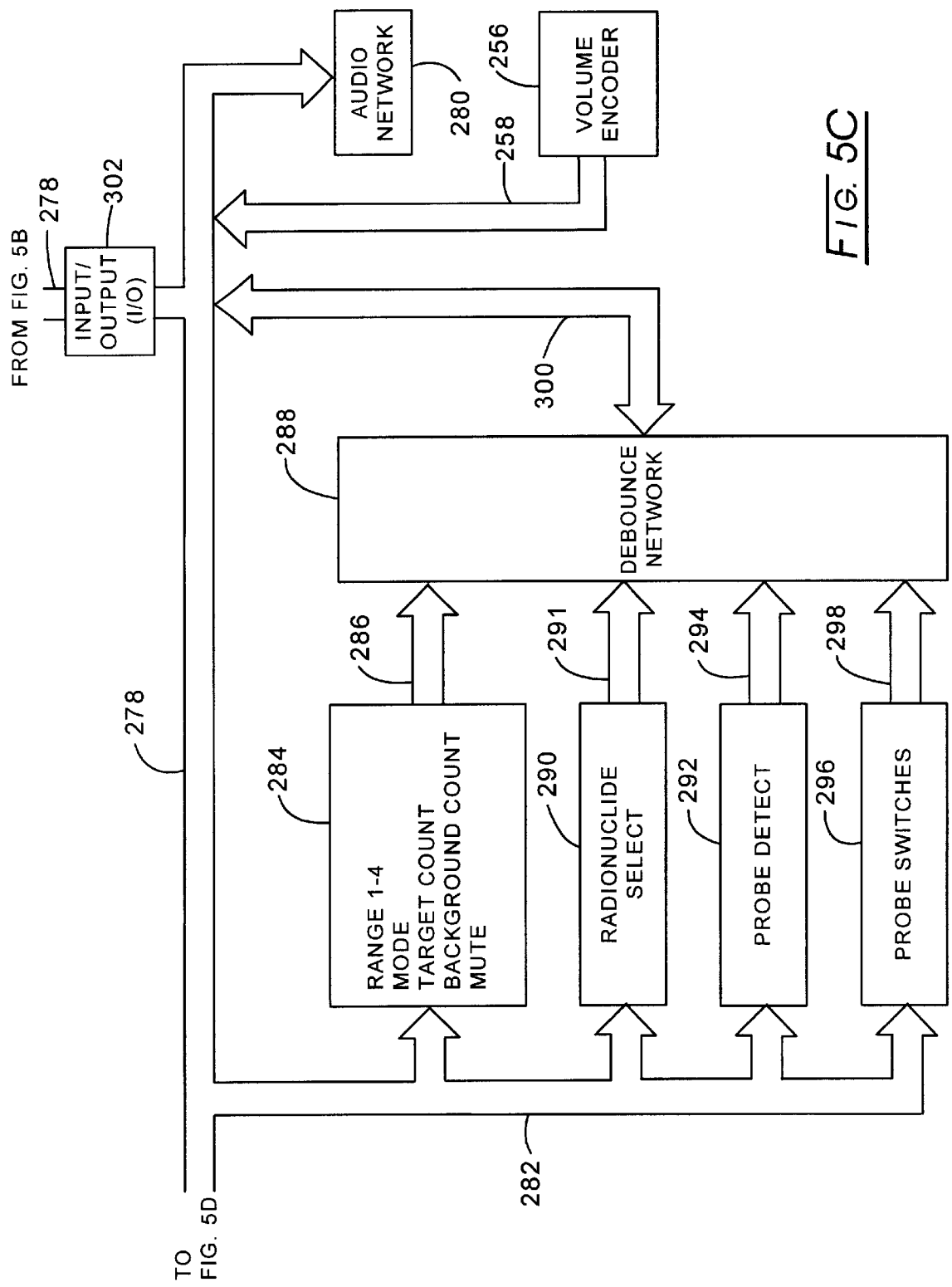

The central processor control function 232 also receives volume data selected by user manipulation of knob 52 (FIG. 1) from an input/output circuit 302 via the bus architecture. The encoding function is represented in FIG. 5C at block 256, while bus related communication is represented at bus arrow 258. Serial port communication also is provided at the central processor control function 232 as represented at block 260 and bidirectional arrow 262. Such communication with the central processor control function 232 permits the reprogramming of system 10 to accommodate future requirements. Control, as represented at arrow 264 also is provided from the central processor control function 232 to a bias selector network represented at block 266 in FIG. 5A. The selector network 266 responds to a digital input to effect the application of a particular bias voltage level at line 201 for presentation to a particular probe as at 12. In general, that bias level will be selected in response to the election by the user of a particular radionuclide. In this regard, it may be recalled that a radionuclide selector switch is provided with the control assembly 22 at its rear housing component 30 and selection of the two most predominating radionuclides is made at switch 54 located at the forward face 40 of assembly 22. These bias levels may be the same for given or selected ones of the radionuclides or may be different depending upon the probe and associated detector architecture. To provide an initial bias voltage supply, an unregulated relatively higher voltage supply as provided at the PDM circuit board 172 is represented in FIG. 5A at block 268. As represented at arrow 270, that bias voltage is delivered to a comparator and current limit network represented at block 272. The comparator network 272 responds to a selection signal from the network represented at block 266 as represented at arrow 274 to develop a predetermined bias level for delivery to the probe interface function represented at block 204 as, in turn, represented at arrow 276.

Referring to FIGS. 5B and 5C, the PC/104 bus architecture is represented at bus arrows 244 and 278 as being in control asserting communication with a variety of switching and user perception associated outputs. As represented at block 280, an audio network is provided which may be a type ES1688 marketed by ESS Technology, Inc. That highly integrated device interfaces directly with the bus architecture of system 10. The network function represented at block 280 includes a speaker and amplifier, the speaker being mounted at the bottom of the rear housing component 30. FIG. 5C identifies the switching functions and probe detection features of the system 10 as they perform in conjunction with the bus 278. In this regard, the bus arrow 278 is seen to branch at 282 for communication with the switches described in connection with FIG. 1. For instance, the range switches 61–64 are associated with the bus; mode switch 54 also is so associated with the bus; target count switch 46 is coupled into the bus architecture; background count switch 48 also is so connected and mute switch 50 is associated with bus 282. These switch functions are represented at block 284 and they further are associated within the bus architecture, as represented at bus component arrow 286, with a switch debounce network represented block 288. The radionuclide select switching function shown at block 290 mounted at the rear housing component 30 also is functionally associated with the bus architecture as represented at 282 through that bus architecture shown as at bus component 291 the bus system provides an input through debounce network 288. System 10 also provides a signal output in the event that probe 12 is inoperative, for example, not being properly connected with the control assembly 22. That probe detect function is represented at block 322 in FIG. 5A in association with arrows 214 and 320. A probe signal is delivered, as represented by arrow 324 to PLD network 230 (FIG. 5B and thence into the bus architecture. The probe detect signal associated with bus component 282 is shown to extend through bus component 294 to the debounce network 288. Finally, the probe 12 may be configured having one or more switches mounted upon its handle. Typically, those switches will emulate target switch 46 and/or background switch 48. Such a switching feature is represented at block 296 in association with the bus architecture 282 and through bus component 298 with the debounce network 288. Debounce network 288 is associated through the bus architecture as represented at bus arrows 300 and 278 with input/output (I/O) network 302. Network 302 additionally is seen associated with the bus architecture bus component 278. The I/O network 302 is mounted upon the I/O board 182 described in connection with FIG. 4.

Looking to FIG. 5D, the bus architecture component 278 is seen to continue its association with a variety of display features. These displays are illuminated with LED arrays under control ultimately of the central processor control function represented at block 232. One count display such as that represented at 92 in FIG. 2 associated with the background count is represented in FIG. 5D at block 306. Positioned upwardly from that display is a ratio value display which is represented at block 308. In general, the ratio display is provided in conjunction with the target count development which, it may be recalled, requires a six second count reading when system 10 is operating under the RIGS mode. No such ratio display is provided during the shorter duration target check associated with switch 46. The bar graph and radionuclide display is represented at block 310 to facilitate user perception, the lowermost and uppermost segments of the 16 segment bar code display are illuminated in a different color than the other segments, for example, they may be illuminated in an amber color while the intermediate segments are illuminated in a green coloration. A "cumulative" count value display is that associated with the output described in 80 in FIG. 2 and is represented herein at block 312. A mode display is represented at block 314. That mode display is one of those visually perceptible outputs at 56 or 58 as shown in FIG. 2. The icon displays including icons representing target count, ratio, background count, mute and probe detect are represented at block 316. Finally, a range display as associated with perceptible display outputs 66–69 is represented at block 318. In general, all of these LED arrays are supported from the forward surface of the backplane or mother board 150 (FIG. 4).

Referring to FIGS. 6A–6D, an electrical schematic diagram of the components supported upon the PDM circuit board described in FIG. 4 at 172 is provided. These figures should be considered in the orientations represented by the labeling thereon. Looking to FIG. 6A, a probe terminal connector J1 is shown representing the probe interface function at block 204 in FIG. 5A. Connector J1 is electrically associated with the probe 12 and is connected with line 340 which conveys the probe signal or pulsed output from the probe 12. Additionally provided at connector J1 is the probe ground represented at line 342, +12 volt power provided from line 344, probe bias provided at line 346 and an optional two lines 348 and 349 which carry signals from any switches which may be mounted upon the handle of the probe 12. Lines 348 and 349 extend to a connector J2 which, in turn, is coupled to the input/output (I/O) function represented in FIG. 5C at block 302. That same I/O function ultimately is connected with the central processor control described in connection with block 232.

Returning to line 340, the EMF filtering function 208 now is represented as an R-C filter comprised of resistor R1 and a capacitor C1. From a filter function 208, the pulse output is directed to a unity gain buffer stage 212 comprised of operational amplifier 350 configured with a network formed with resistors R2–R5 to provide a buffered pulse output at line 352 which will contain a d.c. term. That d.c. term essentially is removed by an a.c. coupling capacitor C2, whereupon the pulsed signal with d.c. term removed is directed via line 354 to one input of an operational amplifier 356, the function of which was earlier described at block 220 in FIG. 5A. Amplifier 356 is configured with resistors R6 and R7 to provide a gain of 2.5. This gain provides for an increase in height of the pulse characterized signal at line 354 to conform the pulse height with the circuitry downstream. Looking additionally to FIG. 6B the pulse signal carrying output of amplifier stage 220 is provided at lines 358, 360 and 362 for simultaneous presentation to the upper and lower energy window comparator network 226. In this regard, line 362 is seen to incorporate a resistor R8 and extend to line 364 which in turn is directed to the one input of an upper energy limit comparator 366. The reference input to comparator 366 emanates from line 368 incorporating a resistor R9. At such time as a pulse signal exceeds the reference established from line 368, a corresponding comparator signal is presented at output line 370. Comparator 366 additionally is configured with resistor R10 located between lines 364 and 370. A pull-up resistor R11 as well as resistor R12 are connected with line 370. Pull-up resistor R11 is seen coupled to +5V. In similar fashion, the amplified pulse signal at line 358 is directed via resistor R13 and line 372 to the input of an comparator 374. The opposite input to comparator 374 is presented from line 376 incorporating a resistor R14. Comparator 374 detects pulses passing a lower threshold reference from line 376 which, for convenience, preferably is established at ground or zero value. The output of the comparator 374 is presented at line 378 and the comparator is seen to be configured with a resistor R15 between line 372 and line 378. A pull up resistor R16 is seen coupled between line 378 and +5V, while the line further incorporates a resistor R19. The signal line 378 is used both for developing output when a pulse asserted from line 358 exceeds the threshold at line 376 and the signal additionally is utilized to measure or compute a pulse width value through utilization of a counting function.

Figure 6A:
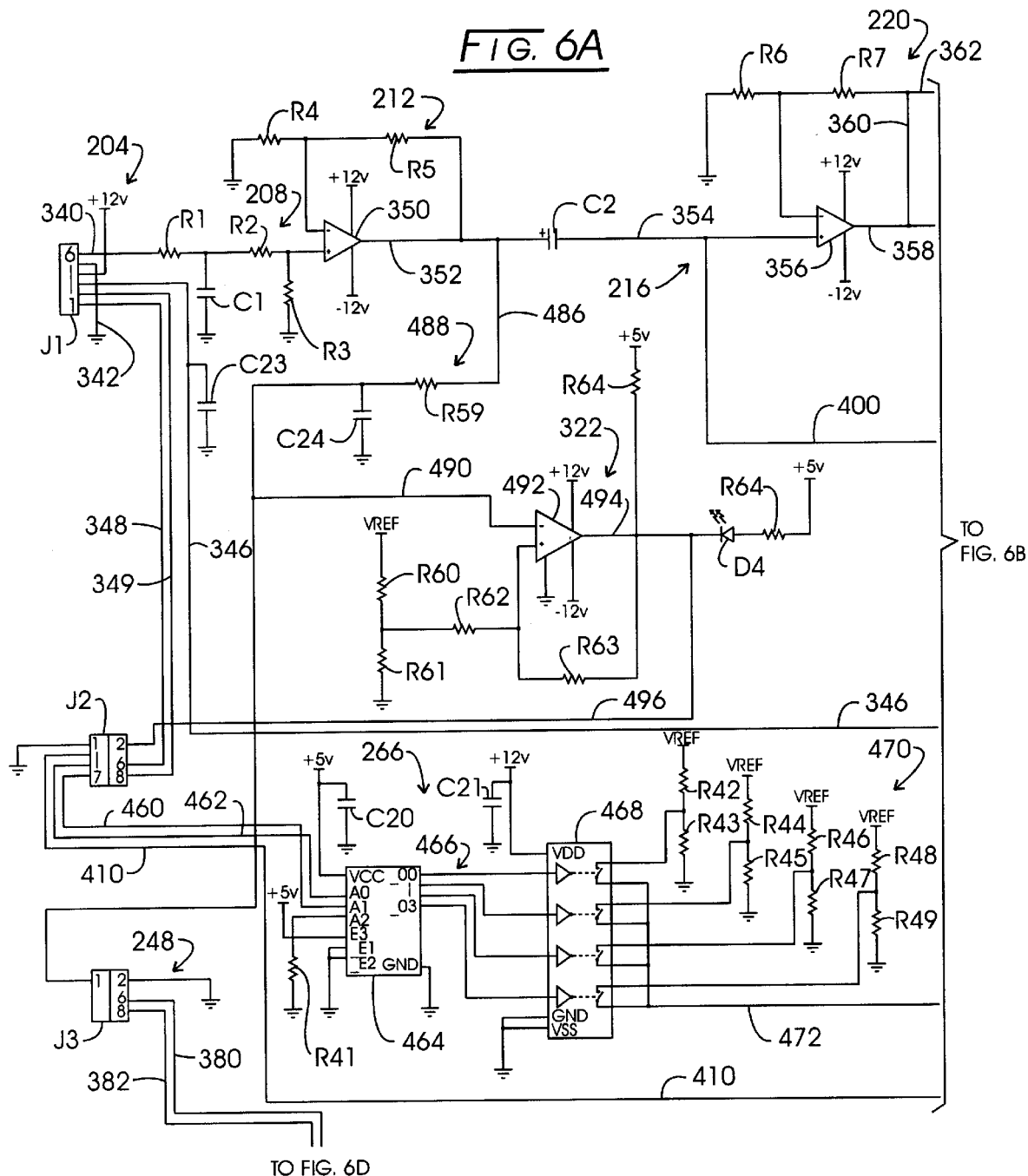
FIGS. 6A–6D combine as labeled thereon to provide an electrical schematic diagram of the circuitry mounted upon a pulse detector module circuit board employed with the console of FIG. 1.
Figure 6B:
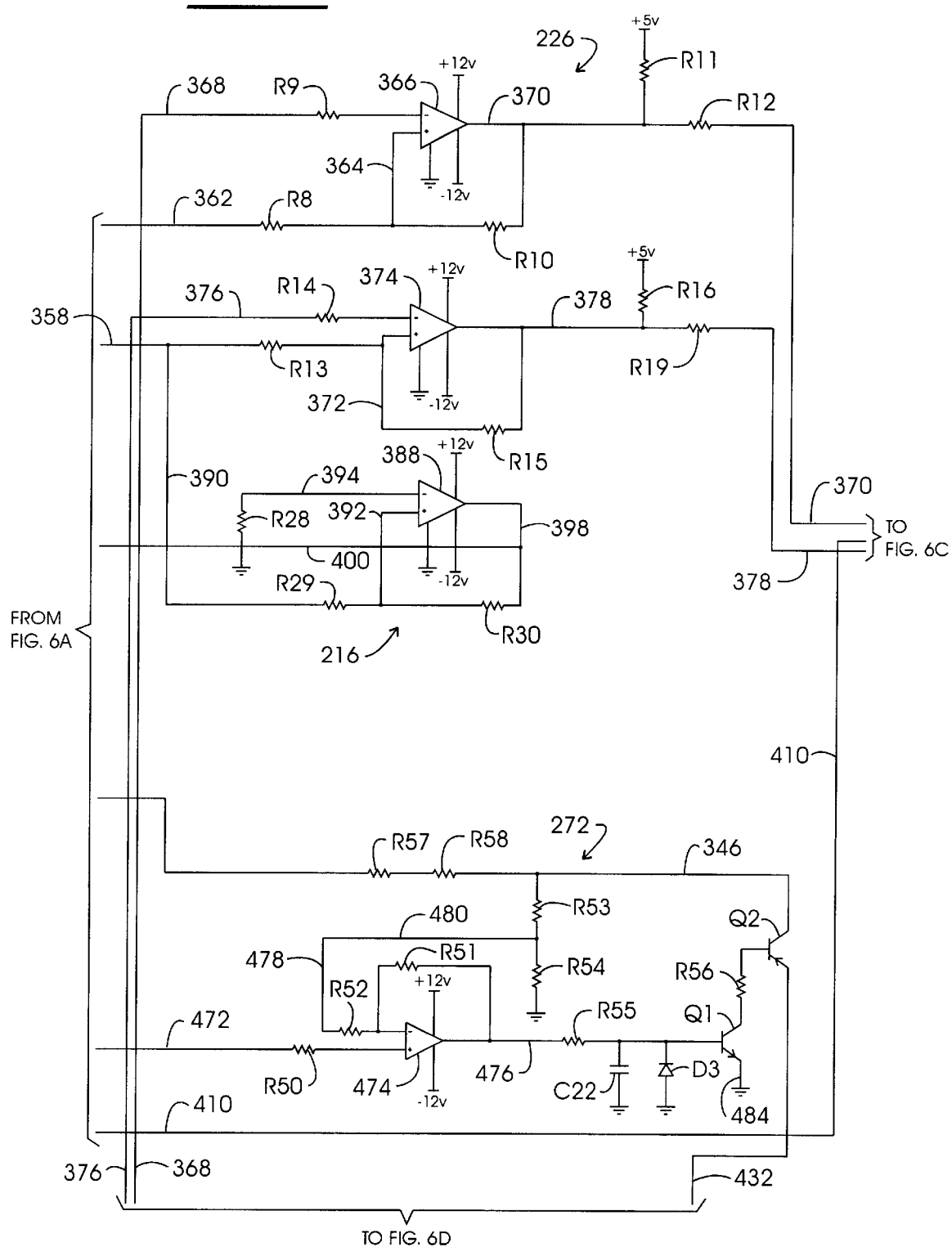

Returning momentarily to FIG. 6A, a connector J3 is revealed. This connector J3 is in electrical communication with the DSP circuit board 178 described in connection with FIG. 4. That particular DSP carrying circuit board also includes two digital-to-analog converters which are employed for the purpose of developing the reference signals ultimately presented at lines 368 and 376. Accordingly, analog reference outputs are seen extending from connector J3 at lines 380 and 382. Referring additionally to FIG. 6D lines 380 and 382 reappear as do lines 376 and 368 which extend to the reference input of respective window comparator 374 and 366. While the analog reference voltage inputs at lines 380 and 382 are quite close to the appropriate reference settings, their values are perfected or masked in conjunction with a precision reference, VREF. In general, under control of the central processor control represented at block 232, window adjustment may be made in correspondence with a selected radionuclide for example, between 0 kev and as high as 600 kev. Accordingly, gamma energy window threshold and upper limits are set automatically in response to the selection of radionuclide. In FIG. 6D, line 380 is seen to extend to one side of a operational amplifier 384. The opposite input to operational amplifier 384 is derived from the noted precision reference, VREF in conjunction with a resistor configuration including resistors R20–R23, resistors R20 and R21 providing a divider function. The output of device 384 is at the earlier-noted line 376 extending to the reference input of lower threshold comparator 374.

In similar fashion, operational amplifier 386 receives the computer controlled analog input from line 382 and performs with the precision reference voltage VREF. The device, is configured with resistors R24 through R27, resistors R24 and R25 providing a dividing function. The output of operational amplifier 386 is at line 368, extending to the reference input of upper limit window comparator 366.

Returning to FIG. 6B the operative components of the earlier-described time-dependent baseline restoration function discussed in connection with block 216 are revealed. In this regard, a comparator 388 is provided having an input coupled to receive the amplified pulse signal from line 358 via lines 390 and 392. The opposite input to device 388 is provided from line 394 which is coupled to ground through a resistor R28. The output of open collector device 388 is provided at line 398 and line 400, the latter line extending, as seen in FIG. 6A to the output side of a.c. coupling comparator C2. Resistors R29 and R30 are positioned within line 398. With the arrangement shown, a soft clamp to ground is imposed at line 354 from line 400 in the absence of a pulse, the restoration approach, essentially discharging operational amplifier C2 in the absence of a pulse signal. With the arrangement, there is no downward drift of the pulse train at higher frequencies as it is coupled from comparator C2.

Figure 6C:
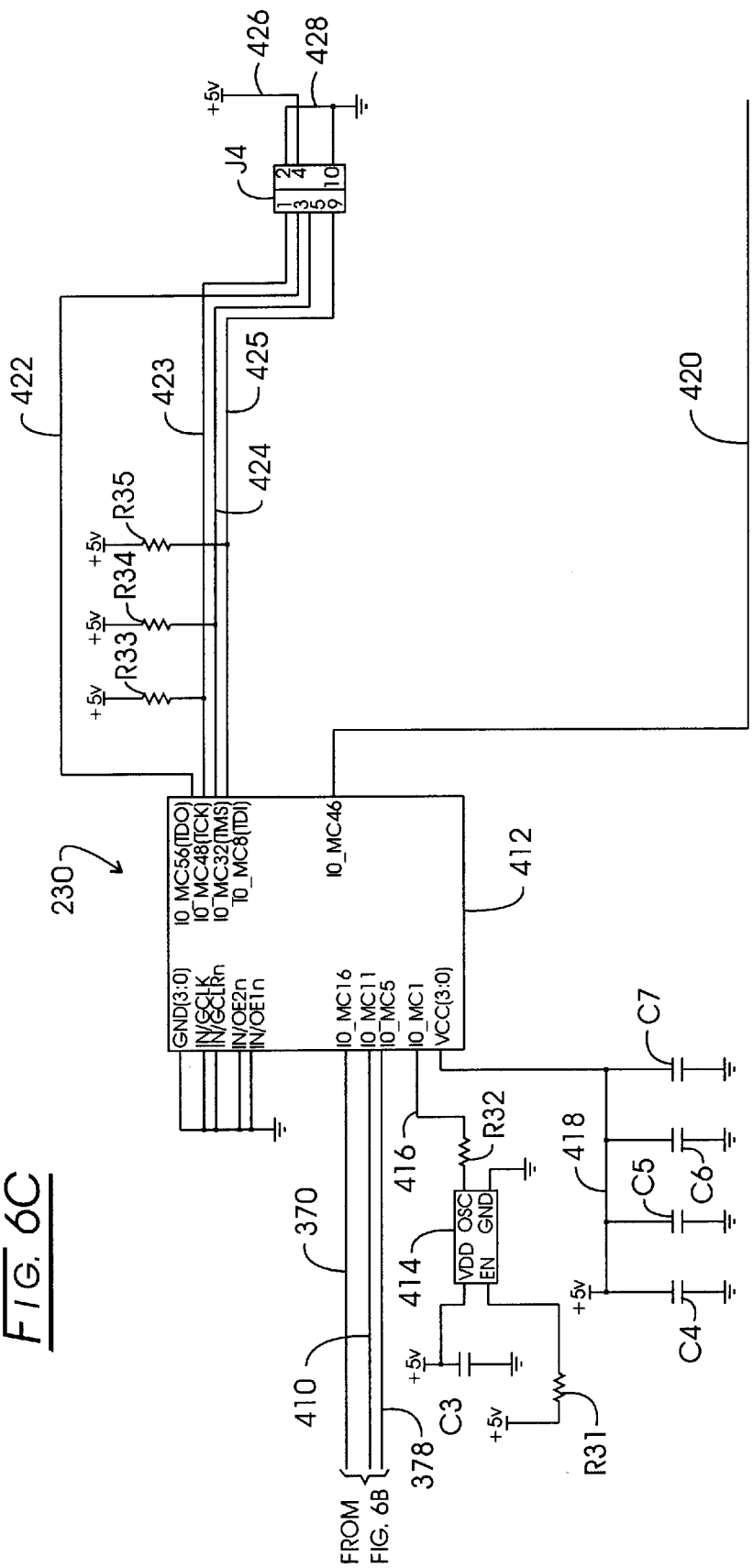
Figure 6D:
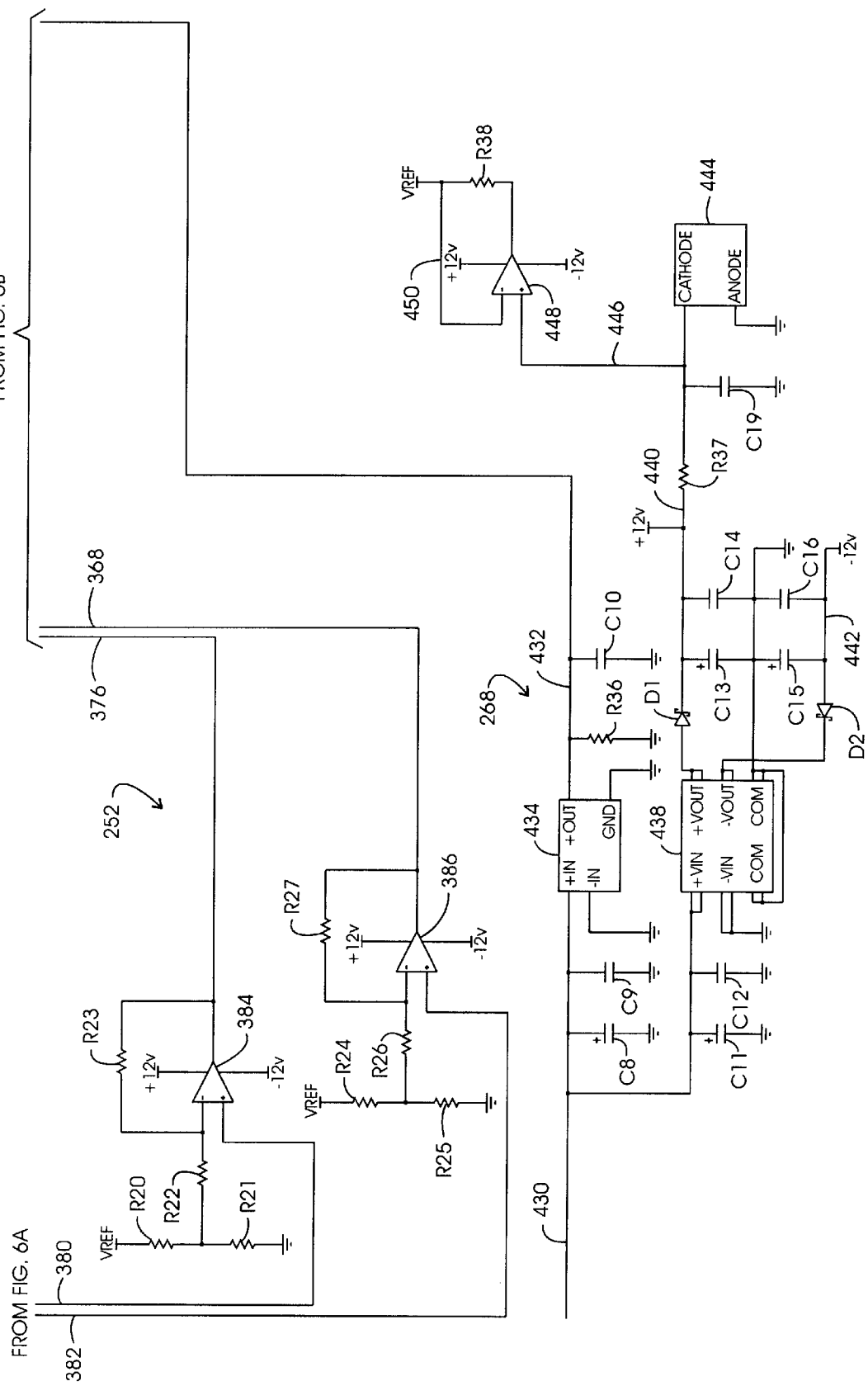

Referring to FIG. 6C, the energy and pulse width discriminator network as discussed in connection with block 230 is revealed. In the figure, line 370 carrying a signal indication that a pulse has exceeded the upper limit of the window function along with line 378 which may carry a signal both describing the width of a pulse passing the lower threshold and the presence of such passage, are applied to a programmable logic device (PLD) 412 along with a control input from the central processor control described in conjunction with block 232. In this regard line 410 extends to connector J2 shown in FIG. 6A which, in turn, extends to the I/O function 302 (FIG. 5C) and the central processor control 232. Device 412 may be provided as a type EPM7064SC-10 and operates in conjunction with an oscillator 414 providing a 20 MHz output and configured with resistors R31 and R32 as well as a comparator C3. The output of the oscillator 414 is provided at line 416. +5V input to the device 412 is provided from line 418 to which are connected filtering comparator C4–C7. Device 412 determines the validity of incoming pulses with a logic which accepts those pulses which have not exceeded the upper limit and have passed the lower threshold of the windowing function described in connection with block 226. This is logically ANDed with a determination of proper width of the incoming window validated pulse. In this regard, studies have shown that a pulse exceeding about 12 microseconds will statistically be invalid or construction noise thus, there is a pulse width discrimination function logically ANDed with the windowing function to provide a valid pulse output at line 420. Line 420 extends to the digital signal processing function described above in connection with block 238. At that function, count rate values, statistical analysis and the like are performed by system 10. PLD 412 may be programmed from an external location via terminal J4. In this regard, lines 422–425 extend from terminal J4 to device 412. Of these lines, lines 423–425 are connected through respective pull up resistors R33–R35 to +5V. Lines 426 and 428 provide +5V and ground to terminal J4.

Returning to FIG. 6D, a power converter and regulator carried by the PDM circuit board 172 are illustrated. These devices perform in conjunction with a +12V input at line 430 which emanates from the earlier described open frame power supply 152 via backplane 150 (FIG. 4). +12V is converted to a 200 volt supply for use by the bias selection circuit at line 432 by a d.c.—to—d.c. converter 434. Converter 434 is configured in conjunction with filtering capacitor C8–C10 and a resistor R36. The 12 volt supply at line 430 is tapped at line 436 for a presentation to another d.c.—to—d.c. converter 438 which provides a +12V output at line 440 and a –12V output at line 442. These supplies are utilized by the circuitry throughout the pulse detector module circuit board 172. Converter 438 is configured on conjunction with capacitor C11–C16 and diodes D1, D2. Line 440 further is seen to extend through a resistor R37 to a 5 volt reference source 444. Line 440 is filtered by capacitor C19. Line 440 further extends adjacent the device 444 via line 446 to an operational amplifier 448 which is configured with a feedback at line 450 and output at line 452 containing a resistor R38. This provides the precision VREF source with adequate current characteristics.

Returning to FIG. 6A, the bias selector network described in conjunction with block 266 in FIG. 5A is revealed at an enhanced level of detail. Four levels of bias for utilization by probes as at 12 are available with system 10. These may be automatically elected in correspondence with the selection of radionuclide by the user in consequence of signals presented at two lines, 460 and 462 extending from connector J2. Connector J2 extends from the I/O function 302 and, in turn from the central processor control 232. These lines 460 and 462 extend to a three line-to-eight line decoder 464 which is configured in conjunction with capacitor C20 and resistor R41. Depending upon the binary selection value established at lines 460 and 462, one of four lines from the four line array 466 is selected to actuate a corresponding one of the analog switches within analog switching device 468. Device 468 is configured in conjunction with capacitor C21. The corresponding switch outputs of device 468 are each coupled with four cascade interconnected divider resistor combinations shown generally as resistor network 470 and formed of resistors R42–R49. Each resistor pair of the network 470 is coupled to precision VREF and a resultant analog voltage level output is presented at line 472 in dependence upon the switching carried out at device 468. Thus, a reference bias level is established at line 472 in response to a processor control input.

Looking additionally to FIG. 6B, line 472 is seen to be directed through resistor R50 to one input of an operational amplifier 474. That input is a proportional voltage level representing a proportion of the ultimately developed bias supply to the probe 12. Amplifier 474 provides an output at line 476 and is configured in conjunction with resistors R51 and R52 at input line 478. Line 478, in turn, is coupled via line 480 and divider resistors RS3 and R54 to a bias output line 346. Accordingly, a feedback to the amplifier 474 providing for a comparison form of control based upon feedback from the bias voltage actually developed. Output line 476 from amplifier 474 is seen to incorporate a resistor R5 and extend to the base of an NPN transistor Q1. The collector of transistor Q1 is coupled with base resistor R56 to the base of PNP transistor Q2. The emitter of transistor Q1 is coupled to ground via line 484, while the emitter of transistor Q2 is coupled to high voltage carrying line 432 and its collector is coupled to bias line 346. Thus, the input from amplifier 474 controls transistor Q2 through transistor Q1 and thus develops the elected bias at line 346. The capacitor C22 is connected to line 476. This capacitor functions to minimize oscillation in the circuit. A diode D3 also is connected to line 476 for purposes of protecting transistor Q1.

Line 346 seen to incorporate two current limiting resistors R57 and R58, which function for the protection of the user of probe 12. Line 346 is seen to extend, as described in connection with FIG. 6A, to the connector J1 for transmittal of bias voltage to probe 12.

Returning to FIG. 6A, the probe detect feature described in connection with block 322 in FIG. 5A is illustrated at an enhanced level of detail. To provide this signal that a probe is appropriately connected or not appropriately connected, the somewhat raw pulse output signal line 352, containing a d.c. term, is tapped by a line 486. Line 486 incorporates a low pass filter 488 comprised of resistor R59 and capacitor C24. Thus, in effect, the d.c. term is extracted. The signal at line 486 then is directed via line 490 to one input of an comparator 492. Comparator 492 is configured with resistors R60–R63 to provide a logic low true output at line 494 in the event of loss of signal at line 490. This indicates that the probe function is defective. Line 494 is coupled to +5V through resistor R64 and incorporates a light emitting diode D4 which extends through resistor R64 to +5V. Diode D4 provides an aid during circuit diagnostics. Line 494 is coupled via line 496 to connector terminal J2 which, as described above, extends to the I/O function described in connection with block 302 and which signal then is conveyed to the central processing control 232.

Figure 7:
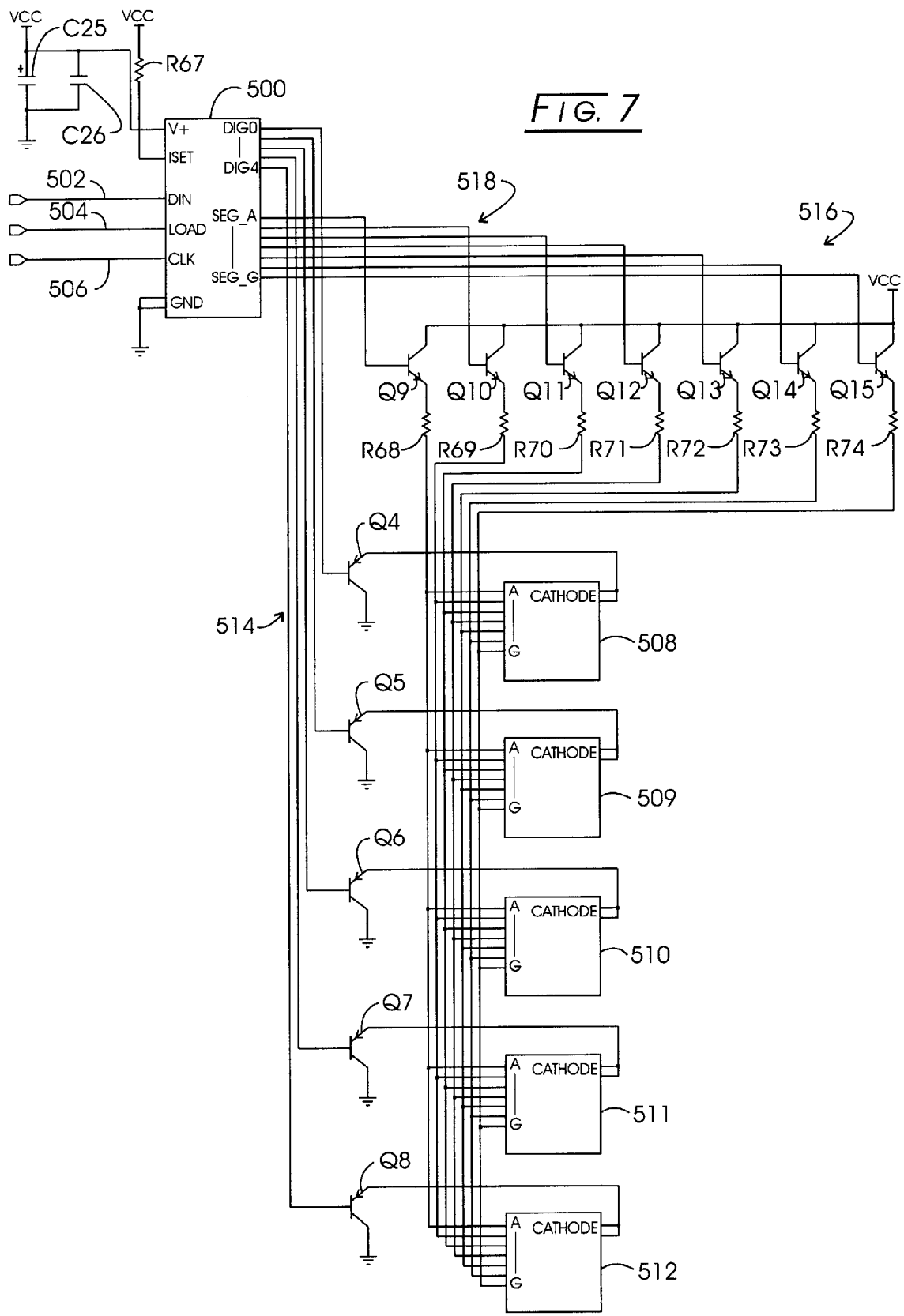
FIG. 7 is an electrical schematic diagram exemplary of display illuminator circuits employed with the console shown in FIG. 1.

As indicated above, the generation of numeric characters and the illumination of icons, as well as the bar graph at window display 42 are carried out with light emitting diode components which are mounted on the forward face of backplane 150. The circuits for driving the display components are quite similar and under the control of the central processing function 232. Accordingly, one such circuit is described in connection with FIG. 7 as exemplary of all those utilized. The circuits feature a very high brightness due to the scanned nature of the operation of them and the scanning procedures carried out such that any quality of brightness is achieved notwithstanding differences in the number of LED components employed. Looking to FIG. 7, the components comprising a small green display generating, for example the background count characters described in conjunction with FIG. 2 at 92 are illustrated. The display utilizes a display controller, for example a type 7219 controller marketed by Maxim, Inc., of Sunnyvale, Ca. This controller is represented in the figure at 500. Controller 500 is configured in conjunction with resistor R67 and capacitors C25 and C26. The device receives a serial data stream from the process control at its data in terminal from line 502. Additionally, a load command is provided from line 504 and a clock input is provided from line 506. In general, the scanned display controller 500 will receive a clock input of between 500 and 600 Hz. This permits the LEDs of each character to be driven at a higher level of current than specified along with a cooling down interval between energizations. The result is a brighter output. Controller 500 performs in conjunction with any of a series of common cathode displays herein having seven segments and shown at 508–512. The devices may, for example be type LN516GK. Controller 500 activates or enables one or all of the displays 508–512 by turning on an appropriate one of PNP transistors Q4–Q8 from line array 514.

Controller 500 then controls the activation of each of the seven segments of each display 508–512 from an array 516 of NPN transistors Q9 . Q15. Note, in this regard, that the collectors of these transistors are commonly coupled to Vcc and the base thereof are coupled to controller 500 from line array 518. The collectors of these transistors are connected to common segment components of the displays 508–512 through resistors R68–R74 which, in turn, are connected with the emitters of respective transistors Q9–Q15.

Figure 8A:
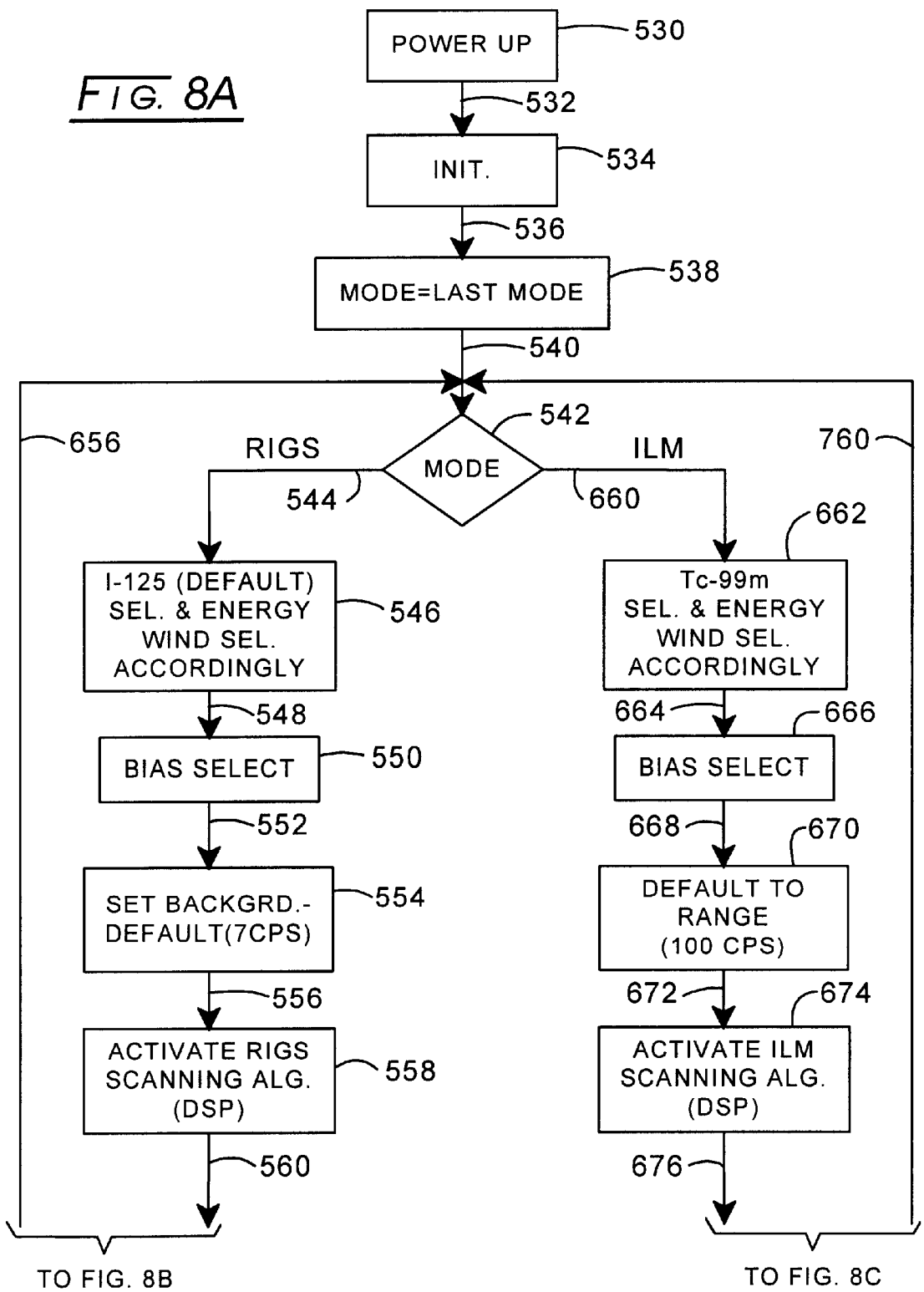
Figure 8B:
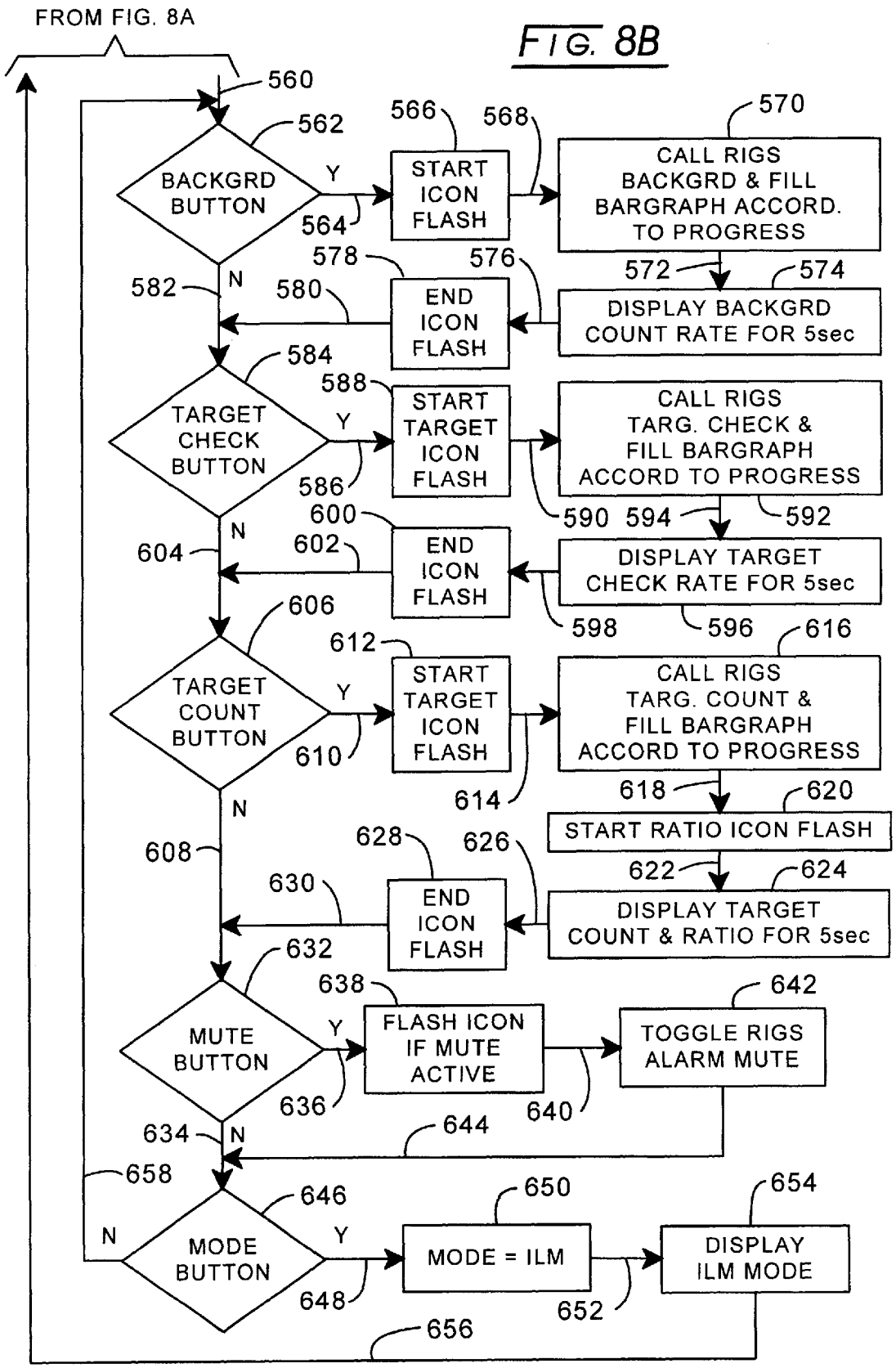

Referring to FIGS. 8A–8C, a flow chart illustrating the main program executed by central processor control 232 as it performs in conjunction with DSP processing function 238 is revealed. The program commences as represented at block 530 with the carrying out of power up. In general, this occurs with the actuation of power switch 44. Then, as represented at line 532 and block 534 initialization procedures are carried out. For these procedures, default values are acquired. If the probe detect function 322 indicates a non-connected probe 12, then 99 is illuminated at display window 42. The program then continues as represented at line 536 and block 538 to default to the last operational mode utilized. In this regard, the two modes concerned at this juncture are the ILM mode and the RIGS mode. For the present flow chart, only those modes are considered. The program then continues as represented at line 540 and block 542 to enter the mode elected. Should the user have changed modes by actuation of switch 54, then that election will be present at this juncture in the program. For either mode, probe 12 is "scanned" along a region of interest. The term is intended to encompass all probe movement and stationary positioning occurring during a collection of photon event data. For the instant demonstration, assuming a RIGS mode has been elected, then the program proceeds as represented at line 544. This RIGS mode also is referred to as a "binary pitch" mode of operation. The RIGS mode of operation commences as represented at block 546 with a default selection of the radionuclide $^{125}$I and the computer selects the reference values for the upper limit and lower threshold of the energy window function 226 accordingly. Continuing as represented at line 548 and block 550, program then elects an appropriate bias for the selected radionuclide, in this case $^{125}$I. This is done by submitting information to the bias selector network 266. Then, as represented at line 552 and block 554 a background default value of seven counts per second is acquired. This background count generally will be altered by the practitioner with the actuation of the background count switch or button 48. Following the election of the default background value, as represented at line 556 and block 558 the RIGS scanning algorithm is activated. This algorithm is executed at the DSP processing function 238. In general, that algorithm utilizes a circular buffer form of temporary memory which is employed to collect validated photon event pulses in 50 millisecond time segment intervals. A statistically significant threshold valuation is computed with respect to each of predetermined combinations of those memory segments and where computed count rates exceed the computed threshold values in a predetermined number, then an aurally perceptive output is generated to apprise the surgeon that the probe 12 window 16 is adjacent tissue having a high probability of tumor involvement. After an initial threshold passage at a first statistical evaluation involving three standard deviations, the algorithm reverts to evaluations at a lowered standard deviation value. When the threshold is not met, on predetermined numbers of occasions, then the aural cueing is terminated and the higher statistical valuation is reasserted. The algorithm further retrieves count data from the circular buffer memory on a half second interval basis to publish a "cumulative" count rate as earlier described at 80 in connection with FIG. 2. The program then continues as represented at line 560 which line reappears in FIG. 8B. Looking to that figure, line 560 is seen directed to the decision block 562 wherein a query is made as to whether the background button or switch 48 has been actuated. In the event that it has, then as represented at line 564 and block 566 the background icon as described at 96 in FIG. 2 is caused to commence to flash or be energized intermittently. Then, as represented at line 568 and block 570 the program calls the RIGS background program which carries out a count evaluation for a fixed interval of six seconds and as that six seconds occurs, the bar graph 84 is proportionately filled from its lower segment 86 to its upper segment 87. This gives the surgeon a visual cue as to where in the background evaluation process the system 10 is. The program then continues as represented at line 572 and block 574 to carry out a displaying of the background count rate value at the location shown at 92 in FIG. 2 for a limited interval of five seconds. During the flashing of the background icon, the background count rate location as at 92 provides a dashed display. The program then continues as represented at line 576 and block 578 to end the background icon flashing and, as represented at lines 580 and 582 to continue the program. Line 582 represents a program path followed additionally where the inquiry posed at block 562 results in a negative determination. The program then continues to the query posed at block 584 wherein a determination is made as to whether the target switch or button 46 has been depressed and immediately released to cause commencement of a target check count evaluation. This target check evaluation calls for the collection of count data at a given location for a shorter interval of two seconds. In the event that the target check button condition is at hand, then as represented at line 586 and block 588, the target icon as described at 82 in FIG. 2 is caused to be energized intermittently, i.e. to flash. Then, as represented at line 590 and block 592 the RIGS target check program is called which, as noted, carries out a two second count evaluation. During this two second count evaluation, the bar graph 84 segments are filled from first to last, i.e., from segment 86 to segment 87. This, as before, provides the surgeon with a visual cue as to the status of this procedure. The program then continues as represented at line 594 and block 596 to provide for the display of the count rate developed from the target check procedure at location 80 in window 42. This display is only for a limited interval of five seconds. During the two second interval of collecting data, dashes are displayed at location 80. The program then continues as represented at line 598 and block 600 wherein the icon flashing is terminated at the end of the five second display. As before, the program then continues as represented at lines 602 and 604. Line 604 additionally represents a continuation of the program where the query posed at block 584 results in a negative determination. Line 604 is seen to extend to block 606. At block 606 a query is posed as to whether a target count button actuation at switch 46 has been carried out. This occurs when the operator holds button 46 down for a one second interval. In the event of a negative determination, the program continues as represented at line 608. Where an affirmative determination is made with respect to the query at block 606, then as represented at line 610 and block 612 the target icon as described at 82 in FIG. 2 is intermittently energized or caused to flash. Then, as represented at line 614 and block 616 the RIGS target count program is called to carry out a six second target count. During this six seconds, the segments of the bar graph 84 are illuminated from first to last or filled so as to apprise the surgeon as to the progress of this procedure. The program then continues as represented at line 618 and block 620 to cause a ratio icon as described at 78 in FIG. 2 to flash. Then, as represented at line 622 and block 624, the target count rate is displayed at location 80 as described in FIG. 2. Additionally, the ratio of the target count to the current background count is computed and displayed at location 76 at display window 42. These displays of target count and ratio values are transitory, being limited to an interval of 5 seconds. The program then continues as represented at line 626 and block 628 wherein at the termination of the five second display interval, the energization of the two pertinent icons is terminated. The program then continues as represented at lines 630 and 608. Line 608 is seen directed to the query posed at block 632 wherein a determination is made as to whether the mute button 48 has been pressed. In the event that it has not, then the program continues as represented at line 634. In the event of an affirmative determination with respect to the query posed at block 632, then the program continues as represented at line 636 and block 638. If the mute condition is active, then a mute icon described at 94 in FIG. 2 is energized intermittently or flashed. The program then continues as represented at line 640 and block 642 wherein the RIGS alarm mute function is toggled. In this regard, an aural feedback representing the mere pushing of a switch button remains active in the system. However, all RIGS aural cueing is suppressed. The program then continues as represented at lines 644 and 634. Lines 634 is seen directed to the query posed at block 646 wherein a determination is made as to whether the mode selection switch or button 54 has been pressed. In the event that it has, then as represented at line 648 and block 650 the mode of system 10 is altered to an ILM mode and, is represented at line 652 and block 654, the ILM mode display 58 is illuminated. As represented at line 656 which continues into FIG. 8A the program loops to line 540 to commence an ILM mode of performance. In the event of a negative determination with respect to the query posed at block 646, then as represented at line 658 the program loops to line 560 to evaluate which actuation on the part of the operator.

Figure 9:
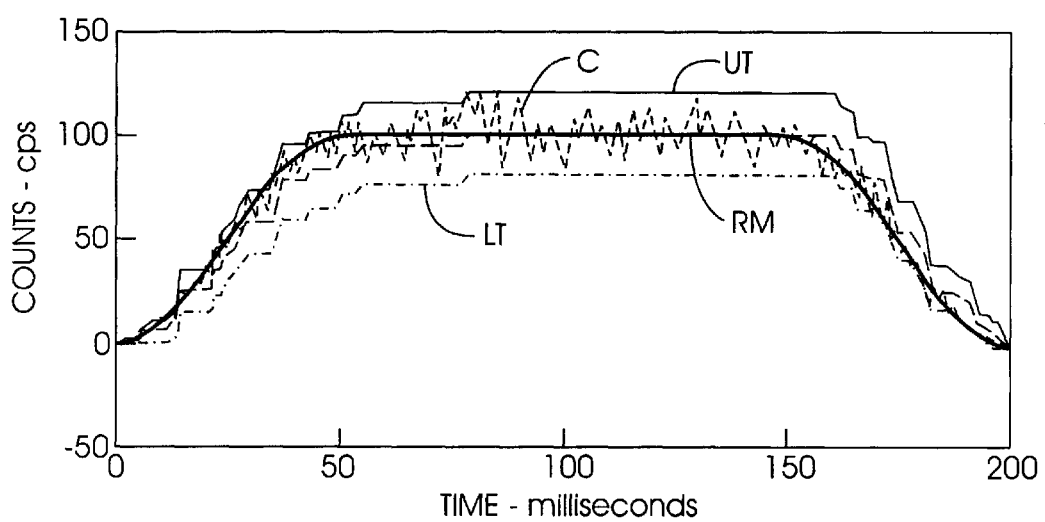
FIG. 9 is a graph illustrating the performance of a floating window form of ILM count evaluation.

Returning to FIG. 8A, where the program enters into an ILM or "dynamic pitch" mode of operation, as discussed above in connection with block 542, then as represented at line 660 and block 662, the radionuclide $^{99m}$Tc is elected and the program selects the appropriate reference levels for the upper limit and lower threshold energy windowing function 226. The program then continues as represented at line 664 and block 666 to select the appropriate bias at the bias selector network 266 for the radionuclide at hand. Then, as represented at line 668 and block 670 default is made to an initial range of 10 to 1000 counts per second. The program then continues as represented at line 672 and block 674 to activate the ILM scanning algorithm, which algorithm is performed at the DSP processing function 238. In general, this algorithm employs a floating window form of analysis in conjunction with temporary memory implemented as a circular buffer memory. The floating memory approach provides a stability of both sound and visual output at the bar graph 84. Looking momentarily at FIG. 9, the floating memory approach is illustrated. In the figure, time in milliseconds is plotted against counts in cycles per second for a probe scan which transverses over a region of higher radiation value. The random counts, c are represented by the dashed curve which is labeled with that variable. Note that the rate increases toward the middle of the plot and decreases at either end. A floating window is continuously computed on a timed basis and is seen to have an upper edge labeled UT and a lower edge which is labeled LT From a computed upper edge UT, a reported mean is calculated and is shown as a solid line in the figure labeled RM. It is this reported mean, RM, which is utilized to generate a sound of varying pitch which elevates as the count rate increases. To accommodate for practitioners who are tone deaf, the frequency excursions are developed from one discrete pitch step to the next. In general, the pitch varies from 300 Hz to 1200 Hz. The same reported mean, RM is used to drive the bar graph 84. It may be observed that the vertical width of the window defined between UT and LT in FIG. 9 varies in correspondence with the count rate level.

Returning to FIG. 8C line 676 reappears leading to the query posed at block 678 determining whether the background button or switch 48 has been depressed. In the event that it has not, then the program continues as represented at line 680. In the event of an affirmative determination, as represented at line 682 and block 684, the background count icon 96 is intermittently energized or flashed and, as represented at line 686 and block 688, the ILM background routine is called. Further, bar graph 84 is energized in accordance with the amount of time required to achieve a background count. In order to expedite the interval for counting, the background count is developed from a predetermined number of count data points representing a corresponding confidence level. Thus, where a higher count frequency is witnessed, the background count will be achieved in a relatively shorter interval of time for example, less than a maximum interval of six seconds. Bar graph 84 will fill by sequentially energizing the LED segments thereof from 86 to 87 in a predicted time interval. However, the interval for filling the bar chart and developing background count is bounded by a minimum interval of two seconds and a maximum interval of six seconds. The program then continues as represented at line 690 and block 692 whereupon the developed background count is displayed at the character location 92 shown in FIG. 2. That display is present for the limited time interval of five seconds. At the termination of five seconds, as represented at line 694 and block 696, the flashing of the background icon 96 is terminated and, as represented at lines 698 and 680 the program continues.

In general, the cumulative ILM count rate is published at display location 80. That count rate is developed from circular memory and is updated each one half second.

Line 680 is seen to be directed to the query posed at block 700 where a determination is made as to whether the target count button 46 has been depressed. It may be recalled that this actuation is one requiring the operator to hold button 46 down for one second. In the event of a negative determination, the program continues as represented at line 702. In the event of an affirmative determination at block 700, then as represented by line 704 and block 706 the target icon 82 is intermittently energized or flashed and, as represented at line 708 and block 710 the ILM target count routine is called. Further, the bar graph 84 is filled utilizing the bounded predictive technique described in connection with block 692. When the target count has been developed, then as represented at line 712 and block 714 the target count is displayed at location 80 as seen in FIG. 2 for the finite interval limited to five seconds. The program then continues as represented at line 716 and block 718 to terminate the flashing icon 82 at the termination of the noted five seconds. The program then continues as represented at lines 720 and 702. The program next proceeds to determine whether the mute button 50 has been pressed as represented at block 722. In the event the mute button 50 has not been actuated, then the program continues as represented at line 724. However, where the button has been pressed, then as represented at line 726 and block 728 the mute icon 94 is energized intermittently or flashed and the program continues as represented at line 730 and block 732 wherein the dynamic pitch count output for the ILM program is turned off. However, an aural feedback "beep" is maintained for any switch actuation. The program then continues as represented at lines 734 and 724.

The program next proceeds to the query posed at block 736 wherein a determination as to whether any of the buttons or switches of the range switch array 60 have been pushed or actuated. In the event they have not, then the program continues as represented at line 738. In the presence of an affirmative to that query, determination then as represented at line 740 and block 742 the dynamic pitch or sound output for the ILM program is altered to provide full scale output for the range selected. This same change is made with respect to the operation of bar graph 84. This alteration also accommodates for any initial threshold value and background value. In particular, typically a 2% threshold is invoked for each of the ranges represented at the switch array 60. Next, as represented at line 744 and block 746 the pertinent range display is illuminated. These displays are shown in FIG. 2 at 66–69. The program then continues as represented at lines 748 and 738 to the query posed at block 750 wherein a determination is made as to whether the mode switch or button 54 has been actuated. In the event that it has, then as represented at line 752 and block 754, the program enters the RIGS mode and, as represented at line 756 and block 758 the RIGS mode display 56 is illuminated. The program then returns, as represented by line 760, to line 540 at FIG. 8A. Where the inquiry at block 750 results in a negative determination, then as represented at loop line 762, the program returns to line 676.

Since certain changes may be made in the above-described system and apparatus without departing from the scope of the invention herein involved, it is intended that all matter contained in the description thereof or shown in the accompanying drawings shall be interpreted as illustrative and not in a limiting sense.

What is claimed is:

1. A system for detecting and locating sources of radiation associated with a locator at a region of interest within an environment evidencing background radiation, comprising:
   a probe moveable within said region of interest and having a pulsed output corresponding with radiation from said source;
   a control assembly having a perceptible output including a display responsive to a first count rate value signal to provide a first perceptible count rate output, responsive to a second count rate value signal to provide a second perceptible count rate output, responsive to a third count rate value signal to provide a third perceptible count rate output, responsive to a graph signal to provide a perceptible bar graph output with segments energizable from first to last, and said control assembly supporting a target count switch actuable to derive first and second target count signals;
   a signal treatment circuit responsive to said probe pulsed output to carry out a validation thereof and derive a count signal; and
   a processing circuit responsive to said count signal and a first predetermined interval to derive said first count rate value signal, responsive to said first target count signal and a second interval to derive said second count rate value signal, and for deriving said graph signal sequentially energizing said segments from first to last in correspondence with said derivation of said second count rate value signal.

2. The system of claim 1 in which said second interval is about two seconds.

3. The system of claim 1 in which said first interval is about one half of a second.

4. The system of claim 1 in which said processing circuit is responsive to said second target count signal and a third interval to derive said third count rate value signal, and for deriving said graph signal sequentially energizing said segments from first to last in correspondence with said derivation of said third count rate value signal.

5. The system of claim 4 in which said third interval is about six seconds.

6. The system of claim 1 in which:
   said control assembly display is responsive to a background count rate signal to provide a visually perceptible background count rate output corresponding with said background radiation, said assembly supporting a background count switch actuable to derive a background signal; and
   said processing circuit is responsive to said count signal in response to said background signal to derive said background count rate signal.

7. The system of claim 6 in which:
   said processing circuit is responsive to said first count rate value signal and to said background count rate signal to derive a said graph signal sequentially energizing said segments from said first segment in correspondence with the difference between the count rate value of said first count rate signal and the count rate value of said background count rate signal.

8. The system of claim 6 in which:
   said control assembly includes an audio network responsive to an audio input to provide an aurally perceptible output and including a mute switch actuable to derive a mute signal; and
   said processing circuit is responsive to said first count rate value signal and to said background count rate signal to generate said audio input when the count rate value represented by said first count rate value signal exceeds the count rate value represented by said background rate signal by a statistically significant amount, and is responsive to said mute signal to block said generation of said audio input.

9. A system for detecting and locating sources of radiation associated with a locator exhibiting a predetermined energy level and located at a region of interest, comprising:
   a probe moveable within said region of interest, having a detector operable under an applied predetermined voltage bias to provide a pulsed output corresponding with radiation from said source;
   a control assembly including:
   a signal treatment circuit responsive to said probe pulsed output to carry out a validation thereof with respect to said predetermined energy level to derive a count signal, a bias voltage circuit connected in bias voltage conveying relationship with said probe and detector and responsive to a bias selection input signal to derive said predetermined voltage bias,
   a radionuclide selector switch actuable to derive a selector switch output representing said locator predetermined energy level;
   a readout assembly responsive to a count rate value signal to provide a perceptible output corresponding therewith; and
   a processing circuit responsive to said count signal for deriving said count rate value signal, and responsive to said selector switch output for deriving said bias selection input signal.

10. A system for detecting and locating sources of radiation associated with a locator at a region of interest evidencing background radiation, comprising:
    a probe movable within said region of interest and having a pulsed output corresponding with radiation impinging thereon;
    a control assembly having a perceptible output including a display assembly, a target count switch actuable to provide a target count signal, and a background count switch actuable to provide a background signal, said display assembly being responsive to a target count rate value signal to display a visually perceptible target count rate value, responsive to a background count rate signal to display a visually perceptible background count rate value, and responsive to a ratio signal to display a ratio value, a signal treatment circuit responsive to said probe pulsed output to carry out a validation thereof and derive a count signal; and
    a processing circuit responsive to said count signal for a background interval in response to said background signal to derive said background count rate signal at the termination of said background interval, responsive to said count signal for a target count interval in the presence of said target count signal to derive said target count rate value signal at the termination of said target count interval, and responsive to derive said ratio signal at the termination of said target count interval in correspondence with the numerical value represented by said target count rate value signal divided by the numerical value represented by said background count rate signal.

11. The system of claim 10 in which said processing circuit provides said target rate value signal for a predetermined interval.

12. The system of claim 11 in which said processing circuit provides said ratio signal for a predetermined finite interval.

13. A system for detecting and locating a radionuclide derived source of radiation exhibiting a predetermined energy level within a region of interest, comprising:
  a probe moveable within said region of interest and having a pulsed output with an amplitude value corresponding with said predetermined energy level;
  a control assembly including:
  a signal treatment circuit responsive to said probe pulsed output, having an energy window network including an upper limit comparator responsive to a select upper limit reference signal and to said pulsed output to provide an upper limit signal when said amplitude value exceeds the value of said selected upper limit reference signal, and further including a lower threshold comparator responsive to a select threshold reference signal and to said pulse output to provide a lower threshold signal when said amplitude value exceeds the value of said select threshold reference signal,
  a discriminator circuit responsive to derive a count signal in response to said lower threshold signal occurring in the absence of said upper limit signal;
  a radionuclide selector switch actuable to derive a selector switch output representing said radionuclide predetermined energy level;
  a readout assembly responsive to a count rate value signal to provide a perceptible output corresponding therewith; and
  a processing circuit responsive to said count signal for deriving said count rate value signal, and responsive to said selector switch output for deriving said select upper limit reference signal and said select threshold reference signal.

14. The system of claim 13 in which:
  said readout assembly includes a display assembly responsive to a radionuclide selection signal to provide a visibly perceptible display representing said radionuclide; and
  said processing circuit is responsive to said selector switch output for deriving said radionuclide selection signal.

15. A system for detecting and locating a source of radiation exhibiting a predetermined energy level within a region of interest comprising:
  a probe movable within said region and having a pulse output with an amplitude value corresponding with said predetermined energy level and a given pulse width;
  a control assembly including:
  a signal treatment circuit responsive to said probe pulse output, having an energy window network including an upper limit network having an upper limit signal when said amplitude value exceeds an upper reference value, and a lower threshold network having a lower threshold signal when said amplitude value exceeds a lower threshold reference value, said lower threshold signal having a signal attribute corresponding with said given pulse width, and
  a discriminator circuit responsive to derive a candidate count signal in response to said lower threshold occurring in the absence of said upper limit signal and responsive to provide said candidate count signal as a validated count signal when said lower threshold signal attributes corresponding with said given pulse width represent a pulse width below a comparative pulse width value representing noise;
  a readout assembly responsive to a count value signal to provide a perceptible output corresponding therewith; and
  a processing circuit responsive to said validated count signal to derive said count value signal.

16. The system of claim 15 in which said comparative pulse width corresponds with a pulse duration of about 12 microseconds.

17. A system for detecting and locating sources of radiation associated with a locator at a region of interest within an environment evidencing background radiation, comprising:
  a probe moveable within said region of interest and having a pulsed output corresponding with radiation from said source;
  a control assembly having a perceptible output including a display responsive to a first count rate value signal to provide a first perceptible count rate output, responsive to a second count rate value signal to provide a second perceptible count rate output, responsive to a third count rate value signal to provide a third perceptible count rate output, responsive to a graph signal to provide a perceptible bar graph output with segments energizable from first to last, said display including a target icon assembly energizable in response to a target icon signal to provide a visually perceptible target icon display, and said control assembly supporting a target count switch actuable to derive first and second target count signals;
  a signal treatment circuit responsive to said probe pulsed output to carry out a validation thereof and derive a count signal; and
  a processing circuit responsive to said count signal and a first predetermined interval to derive said first count rate value signal, responsive to said first target count signal and a second interval to derive said second count rate value signal, for deriving said graph signal sequentially energizing said segments from first to last in correspondence with said derivation of said second count rate value signal, and said processing circuit being responsive to said first target count signal to intermittently derive said target icon signal in response to said second count rate value signal.

18. A system for detecting and locating sources of radiation associated with a locator at a region of interest within an environment evidencing background radiation, comprising:
  a probe moveable within said region of interest and having a pulsed output corresponding with radiation from said source;
  a control assembly having a perceptible output including a display responsive to a first count rate value signal to provide a first perceptible count rate output, responsive to a second count rate value signal to provide a second perceptible count rate output, responsive to a third count rate value signal to provide a third perceptible count rate output, responsive to a graph signal to provide a perceptible bar graph output with segments energizable from first to last, said control assembly supporting a target count switch actuable to derive first and second target count signals, and including a target icon assembly energizable in response to a target icon signal to provide a visually perceptible target icon display;
  a signal treatment circuit responsive to said probe pulsed output to carry out a validation thereof and derive a count signal; and
  a processing circuit responsive to said count signal and a first predetermined interval to derive said first count rate value signal, responsive to said first target count signal and a second interval to derive said second count rate value signal, for deriving said graph signal sequentially energizing said segments from first to last in correspondence with said derivation of said second count rate value signal, said processing circuit being responsive to said second target count signal and a third interval to derive said third count rate value signal, and for deriving said graph signal sequentially energizing said segments from first to last in correspondence with said derivation of said third count rate value signal; and said processing circuit being responsive to said second target count signal to intermittently derive said target icon signal in response to said third count rate value signal.

19. A system for detecting and locating sources of radiation associated with a locator at a region of interest within an environment evidencing background radiation, comprising:

a probe moveable within said region of interest and having a pulsed output corresponding with radiation from said source;

a control assembly having a perceptible output including a display responsive to a first count rate value signal to provide a first perceptible count rate output, responsive to a second count rate value signal to provide a second perceptible count rate output, responsive to a third count rate value signal to provide a third perceptible count rate output, responsive to a graph signal to provide a perceptible bar graph output with segments energizable from first to last, said control assembly supporting a target count switch actuable to derive first and second target count signals, said control assembly display being responsive to a background count rate signal to provide a visually perceptible background count rate output corresponding with said background radiation, said assembly supporting a background count switch actuable to derive a background signal, and said control assembly including a background count icon assembly energizable in response to a background icon signal to provide a visually perceptible background icon display;

a signal treatment circuit responsive to said probe pulsed output to carry out a validation thereof and derive a count signal; and a processing circuit responsive to said count signal and a first predetermined interval to derive said first count rate value signal, responsive to said first target count signal and a second interval to derive said second count rate value signal, for deriving said graph signal sequentially energizing said segments from first to last in correspondence with said derivation of said second count rate value signal, said processing circuit being responsive to said count signal in response to said background signal to derive said background count rate signal, and said processing circuit being responsive to intermittently derive said background icon signal in response to said background signal.

20. A system for detecting and locating sources of radiation associated with a locator at a region of interest within an environment evidencing background radiation, comprising:

a probe moveable within said region of interest and having a pulsed output corresponding with radiation from said source;

a control assembly having a perceptible output including a display responsive to a first count rate value signal to provide a first perceptible count rate output, responsive to a second count rate value signal to provide a second perceptible count rate output, responsive to a third count rate value signal to provide a third perceptible count rate output, responsive to a graph signal to provide a perceptible bar graph output with segments energizable from first to last, said control assembly supporting a target count switch actuable to derive first and second target count signals, said control assembly display being responsive to a background count rate signal to provide a visually perceptible background count rate output corresponding with said background radiation, said assembly supporting a background count switch actuable to derive a background signal, and said control assembly including an audio network responsive to an audio input to provide an aurally perceptible output and including a mute switch actuable to derive a mute signal;

a signal treatment circuit responsive to said probe pulsed output to carry out a validation thereof and derive a count signal; and a processing circuit responsive to said count signal and a first predetermined interval to derive said first count rate value signal, responsive to said first target count signal and a second interval to derive said second count rate value signal, and for deriving said graph signal sequentially energizing said segments from first to last in correspondence with said derivation of said second count rate value signal, said processing circuit being responsive to said count signal in response to said background signal to derive said background count rate signal, said processing circuit being responsive to said first count rate value signal and to said background count rate signal to generate said audio input when the count rate value represented by said first count rate value signal exceeds the count rate value represented by said background rate signal by a statistically significant amount, and is responsive to said mute signal to block said generation of said audio input.

21. A system for detecting and locating sources of radiation associated with a locator at a region of interest evidencing background radiation, comprising:

a probe movable within said region of interest and having a pulsed output corresponding with radiation impinging thereon;

a control assembly having a perceptible output including a display assembly, a target count switch actuable to provide a target count signal, and a background count switch actuable to provide a background signal, said display assembly being responsive to a target count rate value signal to display a visually perceptible target count rate value, responsive to a background count rate signal to display a visually perceptible background count rate value, responsive to a ratio signal to display a ratio value, said control assembly including a target icon assembly energizable in response to a target icon signal to provide a visually perceptible target icon display;

a signal treatment circuit responsive to said probe pulsed output to carry out a validation thereof and derive a count signal; and a processing circuit responsive to said count signal for a background interval in response to said background signal to derive said background count rate signal at the termination of said background interval, responsive to said count signal for a target count interval in the presence of said target count signal to derive said target count rate value signal at the termination of said target count interval, responsive to derive said ratio signal at the termination of said target count interval in correspondence with the numerical value represented by said target count rate value signal divided by the numerical value represented by said background count rate signal, and said processing circuit being responsive to said target count signal to derive said target icon signal intermittently during said target count interval.

22. A system for detecting and locating sources of radiation associated with a locator at a region of interest evidencing background radiation, comprising:

a probe movable within said region of interest and having a pulsed output corresponding with radiation impinging thereon;

a control assembly having a perceptible output including a display assembly, a target count switch actuable to provide a target count signal, and a background count switch actuable to provide a background signal, said display assembly being responsive to a target count rate value signal to display a visually perceptible target count rate value, responsive to a background count rate signal to display a visually perceptible background count rate value, responsive to a ratio signal to display a ratio value, said control assembly including a background count icon assembly energizable in response to a background icon signal to provide a visually perceptible background icon display;

a signal treatment circuit responsive to said probe pulsed output to carry out a validation thereof and derive a count signal; and a processing circuit responsive to said count signal for a background interval in response to said background signal to derive said background count rate signal at the termination of said background interval, responsive to said count signal for a target count interval in the presence of said target count signal to derive said target count rate value signal at the termination of said target count interval, responsive to derive said ratio signal at the termination of said target count interval in correspondence with the numerical value represented by said target count rate value signal divided by the numerical value represented by said background count rate signal, and said processing circuit being responsive to said background signal to derive said background icon signal intermittently during said background interval.

23. A system for detecting and locating sources of radiation associated with a locator at region of interest evidencing background radiation, comprising:

a probe movable within said region of interest and having a pulsed output corresponding with radiation impinging thereon;

a control assembly having a perceptible output including a display assembly, a target count switch actuable to provide a target count signal, and a background count switch actuable to provide a background signal, said display assembly being responsive to a target count rate value signal to display a visually perceptible target count rate value, responsive to a background count rate signal to display a visually perceptible background count rate value, and responsive to a ratio signal to display a ratio value, said control assembly includes a ration icon assembly energizable in response to a ration icon signal to provide a visually perceptible ratio icon display;

a signal treatment circuit responsive to said probe pulsed output to carry out a validation thereof and derive a count signal; and a processing circuit responsive to said count signal for a background interval in response to said background signal to derive said background count rate signal at the termination of said background interval, responsive to said count signal for a target count interval in the presence of said target count signal to derive said target count rate value signal at the termination of said target count interval, and responsive to derive said ratio signal at the termination of said target count interval in correspondence with the numerical value represented by said target count rate value signal divided by the numerical value represented by said background count rate signal, and said processing circuit is responsive to derive said ratio icon signal at the said termination of said target count interval.

24. A system for detecting and locating a source of radiation exhibiting a predetermined energy level within a region of interest comprising:

a probe movable within said region and having a pulse output with an amplitude value corresponding with said predetermined energy level and a given pulse width;

a control assembly including:

a signal treatment circuit responsive to said probe pulse output, having an energy window network including an upper limit network having an upper limit signal when said amplitude value exceeds an upper reference value, and a lower threshold network having a lower threshold signal when said amplitude value exceeds a lower threshold reference value, said lower threshold signal having a signal attribute corresponding with said given pulse width, said signal treatment circuit including a coupling capacitor responsive to said pulse output to provide a coupled pulse output at its output, and a baseline restoration circuit responsive to said coupled pulse output to clamp said capacitor output to a reference voltage level in the absence of said coupled pulse output, said energy window network is responsive to said coupled pulse output to derive said upper limit signal and said lower threshold signal, and a discriminator circuit responsive to derive a candidate count signal in response to said lower threshold occurring in the absence of said upper limit signal and responsive to provide said candidate count signal as a validated count signal when said lower threshold signal attributes corresponding with said given pulse width represent a pulse width below a comparative pulse width value representing noise;

a readout assembly responsive to a count value signal to provide a perceptible output corresponding therewith; and a processing circuit responsive to said validated count signal to derive said count value signal.

25. The system of claim 24 in which said reference voltage level is electrical ground.

* * * * *